US008697735B2

(12) United States Patent
Kalofonos et al.

(10) Patent No.: US 8,697,735 B2
(45) Date of Patent: Apr. 15, 2014

(54) SOLID FORMS OF EPALRESTAT

(75) Inventors: Isabel Kalofonos, Cambridge, MA (US); G. Patrick Stahly, West Lafayette, IN (US); William Martin-Doyle, Cambridge, MA (US); Dimitris Kalofonos, Cambridge, MA (US); Jeffrey S. Stults, West Lafayette, IN (US); Travis L. Houston, Lafayette, IN (US)

(73) Assignee: Bionevia Pharmaceuticals, Inc., Cambridge, MA (US)

( * ) Notice: Subject to any disclaimer, the term of this patent is extended or adjusted under 35 U.S.C. 154(b) by 463 days.

(21) Appl. No.: 13/013,786

(22) Filed: Jan. 25, 2011

(65) Prior Publication Data

US 2011/0275681 A1 Nov. 10, 2011

Related U.S. Application Data

(63) Continuation-in-part of application No. PCT/US2009/051687, filed on Jul. 24, 2009, which is a continuation-in-part of application No. PCT/US2009/051693, filed on Jul. 24, 2009.

(60) Provisional application No. 61/083,611, filed on Jul. 25, 2008, provisional application No. 61/083,619, filed on Jul. 25, 2008.

(51) Int. Cl.
*A61K 31/426* (2006.01)
*C07D 277/36* (2006.01)

(52) U.S. Cl.
USPC .......................................... 514/369; 548/183

(58) Field of Classification Search
USPC .......................................... 548/183; 514/369
See application file for complete search history.

(56) References Cited

U.S. PATENT DOCUMENTS

| | | | |
|---|---|---|---|
| 3,704,245 | A | 11/1972 | Umio et al. |
| 4,443,469 | A | 4/1984 | Nishizono |
| 4,831,045 | A | 5/1989 | Tanouchi et al. |
| 6,444,665 | B1 | 9/2002 | Helton et al. |
| 6,696,407 | B1 | 2/2004 | Longo et al. |
| 6,936,601 | B2 | 8/2005 | Helton et al. |
| 2005/0181041 | A1 | 8/2005 | Goldman |
| 2011/0275682 | A1 | 11/2011 | Kalofonos et al. |
| 2011/0275695 | A1 | 11/2011 | Kalofonos et al. |

FOREIGN PATENT DOCUMENTS

| | | |
|---|---|---|
| EP | 1106210 A2 | 6/2001 |
| GB | 1247067 | 9/1971 |
| JP | 62-51955 | 9/1994 |
| JP | 2004-210703 | 7/2004 |
| JP | 2005-298424 | 10/2005 |
| JP | 2006-104064 | 4/2006 |
| JP | 2007-099680 | 4/2007 |
| WO | WO 97/23477 | 3/1997 |
| WO | WO 2004/078163 A2 | 9/2004 |
| WO | WO 2009/152347 A2 | 12/2009 |
| WO | WO 2010/011922 A2 | 1/2010 |
| WO | WO 2010/011926 A2 | 1/2010 |
| WO | WO 2010/028132 A2 | 3/2010 |

OTHER PUBLICATIONS

Medicines in Development for Neurological Disorders 2008.*
Schafer et al. Drug Discovery Today 2008, 13 (21/22), 913-916.*
Horig et al., Journal of Translational Medicine 2004, 2(44).*
Baba M., Journal of the Peripheral Nervous System 2003; 8:170.
Balbach, S. et al., Int. J. Pharmaceutics 2004; 275:1-12.
Etter, M.C. et al., J. Am. Chem. Soc. 1990 112 8415-8426.
Goto Y. et al., Diabet Med 1993; 10(suppl 2):S39-43.
Goto Y. et al., Biomed Pharmacother 1995;49:269-77.
Gould, P.L., Int. J. Pharmaceutics 1986, 33:201-217.
Hotta N. et al., J Diabetes Complications 1996;10:168-72.
Hotta N. et al., Diabetes Care 2006; 29:1538-44.
Ikeda T et al., Diabetes Research and Clinical Practice 1999;43:193-198.
Ishida, Toshimasa et al., "Conformation of (Z)-3-Carboxymethyl-[2(E)-2-methyl-3-phenylpropenylidene]-rhodanine (Epalrestat), a Potent Aldose Reductase Inhibitor: X-Ray Crystallographic, Energy Calculational, and Nuclear Magnetic Resonance Studies," J. Chem. Soc. Perkin Trans. 2, pp. 1085-1091 (1990).
Ishida, Toshimasa et al., "Structural Elucidation of Epalrestat (ONO-2235), A Potent Aldose Reductase Inhibitor, and Isomerization of its Double Bonds," Tetrahedron Letters, vol. 30, No. 8, pp. 959-962 (1989).
Kurono, Yukihisa et al., "Photo-Stabilization and Solubilization of an Aldose Reductase Inhibitor, (E)-3-Carboxymethyl-5-[(2E)-methyl-3-phenylpropenylidene]rhodanine (ONO-2235), by Human Serum Albumin," Chem. Pharm. Bull., 35(7), pp. 3045-3048 (1987).
McNamara, D.P., et al., Pharmaceutical Research, 2006; V. 23, No. 8, 1888-1897.
Terashima, Hiroshi et al., "Effects of a New Aldose Reductase Inhibitor on Various Tissues in Vitro," J. Pharmacology and Experimental Therapeutics, vol. 229, No. 1, pp. 226-230 (1984).
Wijekoon, E.P. et al., Diabetes, 2005 ; vol. 5, No. 11, 3245-3251.
International Search Report for International Publication No. WO 2010/011922 A2 (International Application No. PCT/US2009/051687) dated Mar. 3, 2010.
Written Opinion for International Publication No. WO 2010/011922 A2 (International Application No. PCT/US2009/051687) dated Mar. 3, 2010.

(Continued)

*Primary Examiner* — Kamal Saeed
(74) *Attorney, Agent, or Firm* — The Marbury Law Group, PLLC

(57) ABSTRACT

The invention relates to novel crystalline salts of 5-[(1Z,2E)-2-methyl-3-phenylpropenylidene]-4-oxo-2-thioxo-3-thiazolidineacetic acid and a novel betaine cocrystal of 5-[(1Z,2E)-2-methyl-3-phenyl propenylidene]- 4-oxo-2-thioxo-3-thiazolidineacetic acid. The preparation and characterization of the novel crystalline salts and cocrystal according to various embodiments of the invention is described. The invention also relates to pharmaceutical compositions containing the novel crystalline salts and cocrystal and the therapeutic use of the novel crystalline salts and cocrystal to treat and/or prevent various conditions, including treating and/or preventing diabetic complications, inhibiting aldose reductase, and affording cardioprotection in patients who may be non-diabetic.

21 Claims, 31 Drawing Sheets

(56) References Cited

OTHER PUBLICATIONS

International Search Report for International Publication No. WO 2010/011926 A2 (International Application No. PCT/US2009/051693) dated Mar. 3, 2010.
Written Opinion for International Publication No. WO 2010/011926 A2 (International Application No. PCT/US2009/051693) dated Mar. 3, 2010.
International Search Report for International Publication No. WO 2009/152347 A2 (International Application No. PCT/US2009/047060) dated Jan. 18, 2010.
Written Opinion for International Publication No. WO 2009/152347 A2 (International Application No. PCT/US2009/047060) dated Jan. 18, 2010.
International Search Report for International Publication No. WO 2010/028132 A2 (International Application No. PCT/US2009/055868) dated Apr. 28, 2010.
Written Opinion for International Publication No. WO 2010/028132 A2 (International Application No. PCT/US2009/055868) dated Apr. 28, 2010.
Certified English translation of JP2007-99680, dated Dec. 9, 2013.

\* cited by examiner

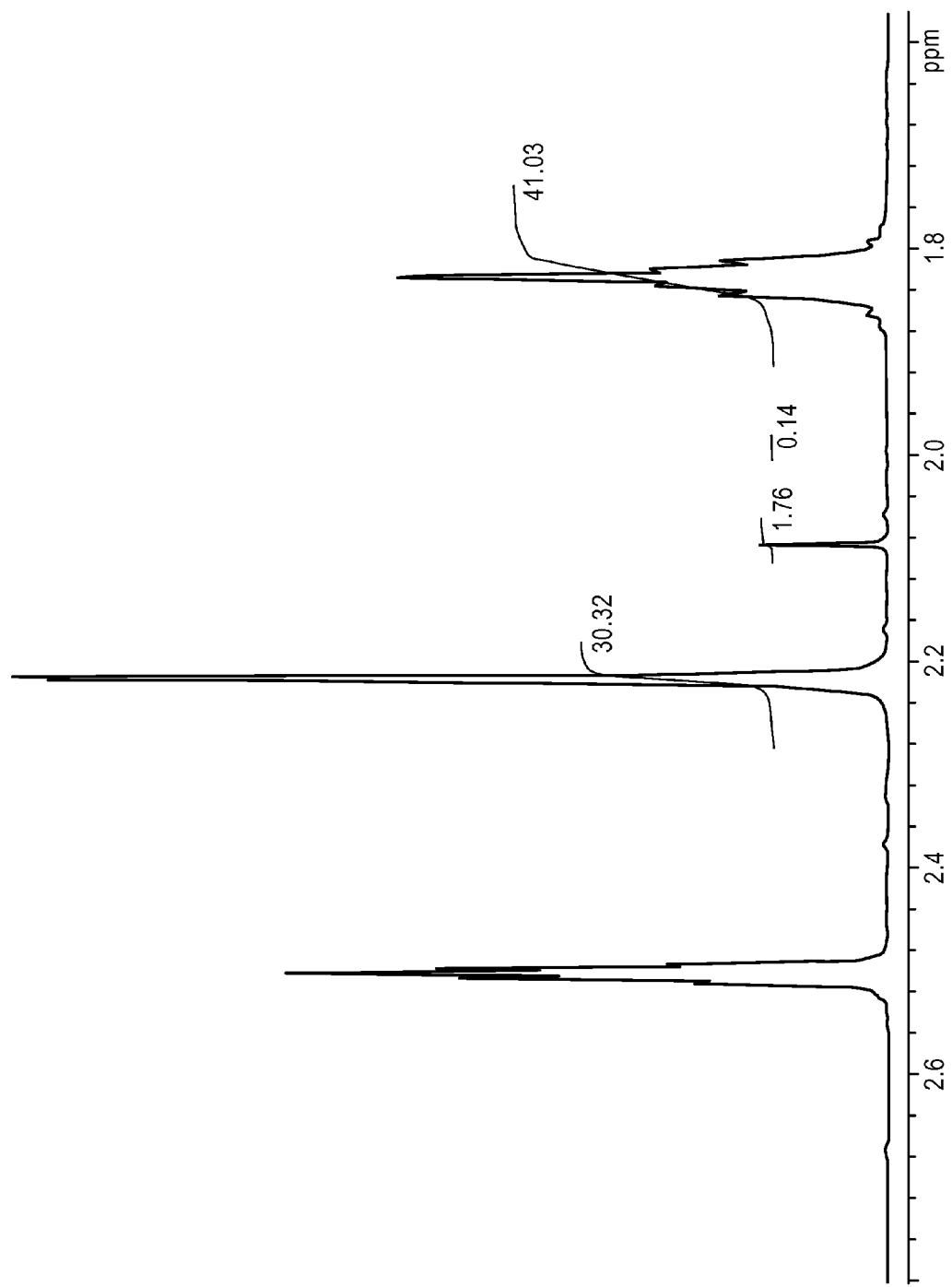

SOLID FORMS OF EPALRESTAT

CROSS-REFERENCE TO RELATED APPLICATIONS

This application is a continuation-in-part of International Application No. PCT/US2009/051687, filed on Jul. 24, 2009, which published in English as WO 2010/011922, and claims priority under 35 U.S.C. §119 to U.S. Provisional Application 61/083,611, filed Jul. 25, 2008, both of which are incorporated herein by reference. This application is also a continuation-in-part of International'Application No. PCT/US2009/051693, filed on Jul. 24, 2009, which published in English as WO 2010/011926, and claims priority under 35 U.S.C. §119 to U.S. Provisional Application 61/083,619, filed Jul. 25, 2008, both of which are incorporated herein by reference.

TECHNICAL FIELD

One aspect of the invention described herein relates to novel crystalline salts of 5-[(1Z,2E)-2-methyl-3-phenylpropenylidene]-4-oxo-2-thioxo-3-thiazolidineacetic acid, processes for making those novel crystalline salts, pharmaceutical compositions comprising those novel crystalline salts, and methods of treating and/or preventing various conditions by administering those novel crystalline salts.

A further aspect of the invention described herein relates to a novel betaine cocrystal of 5-[(1Z,2E)-2-methyl-3-phenyl-propenylidene]-4-oxo-2-thioxo-3-thiazolidineacetic acid, processes for making the novel betaine cocrystal, pharmaceutical compositions comprising the novel betaine cocrystal, and methods of treating and/or preventing various conditions by administering the novel betaine cocrystal.

BACKGROUND

The compound 5-[(1Z,2E)-2-methyl-3-phenylpropenylidene]-4-oxo-2-thioxo-3-thiazolidineacetic acid (shown below), referred to by its common name "epalrestat," is a known active pharmaceutical ingredient ("API") having beneficial therapeutic activity, for example as an aldose reductase inhibitor:

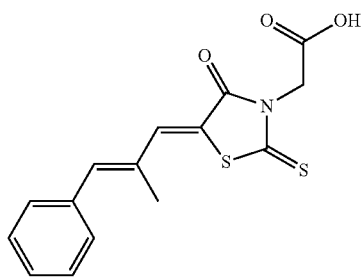 [SMILES: CC(/C=C1\SC(=S)N(CC(=O)O)C1=O)=C\c1ccccc1]

The preparation and pharmacologic activity of epalrestat is described in U.S. Pat. No. 4,831,045. Epalrestat is useful in treating and/or preventing various conditions such as, for example, complications of diabetes, as well as affording cardioprotection in non-diabetic patients. For example, epalrestat has a positive indication for the treatment and/or prevention of diabetic neuropathy, and is useful for the treatment and/or prevention of various other diabetic complications including, for example, diabetic retinopathy, diabetic nephropathy, diabetic cardiomyopathy, diabetic gastroparesis, diabetic microangiopathy, and diabetic macroangiopathy in mammals. Epalrestat is also useful in affording cardioprotection to subjects who may not be suffering from diabetes, and as a neuroprotectant or treatment for neurological or neurodegenerative disorders. Therapeutic activity of epalrestat in various conditions has been demonstrated in the clinical literature, including but not limited to Machii H. et al., Gendai Iryo, 1996; 28:1273; Miyamoto S. et al., Gendai Iryo, 1986; 18 (Extra Issue III):82; Goto Y. et al., Journal of Clinical and Experimental Medicine, 1990; 152:405; Nakano K. et al., Journal of Clinical and Experimental Medicine, 1990; 152: 137; Okamoto H. et al., Internal Medicine, 2003; 42:655-664; Hamada Y. et al., Diabetes Care 2000; 23:1539-44.; Goto Y. et al., Diabet Med 1993; 10(suppl 2):S39-43; Goto Y. et al., Biomed Pharmacother 1995; 49:269-77; Uchida K. et al., Clin Ther 1995; 17:460-6; Hotta N. et al., J Diabetes Complications 1996; 10:168-72; Hotta N. et al., Diabetes Care 2006; 29:1538-44; Matsuoka K. et al., Diabetes Res Clin Pract 2007; 77(suppl 1):S263-8; Nakayama M. et al., Diabetes Care 2001; 24:1093-8; Baba M., Journal of the Peripheral Nervous System 2003; 8:170; Yasuda H. et al., Diabetes Care 2000; 23:705; IkedaT et al., Diabetes Research and Clinical Practice 1999; 43:193-198; Katayama M. et al., Electroencephalography and Clinical Neurophysiology/Electromyography and Motor Control 1995; 97:81; and Misawa S. et al., Neurology 2006; 66:1545-9.

Although therapeutic efficacy is a primary concern for a therapeutic agent, such as epalrestat, the salt and solid state form (e.g. crystalline or amorphous forms) of a drug candidate can be important to its pharmacological properties and to its development as a viable API. For example, each salt or each crystalline form of a drug candidate can have different solid state (physical and chemical) properties. The differences in physical properties exhibited by a particular solid form of an API, such as a cocrystal, salt, or polymorph of the original compound, can affect pharmaceutical parameters of the API. For example, storage stability, compressibility and density, all of which can be important in formulation and product manufacturing, and solubility and dissolution rates, which may be important factors in determining bioavailability, may be affected. Because these physical properties are often influenced by the solid state form of the API, they can significantly impact a number of factors, including the selection of a compound as an API, the ultimate pharmaceutical dosage form, the optimization of manufacturing processes, and absorption in the body. Moreover, finding the most adequate form for further drug development can reduce the time and the cost of that development.

Obtaining pure crystalline forms, then, is extremely useful in drug development. It may permit better characterization of the drug candidate's chemical and physical properties. For example, crystalline forms often have better chemical and physical properties than amorphous forms. As a further example, a crystalline form may possess more favorable pharmacology than an amorphous form, or may be easier to process. It may also have better storage stability.

One such physical property which can affect processability is the flowability of the solid, before and after milling. Flowability affects the ease with which the material is handled during processing into a pharmaceutical composition. When particles of the powdered compound do not flow past each other easily, a formulation specialist must take that fact into account in developing a tablet or capsule formulation, which may necessitate the use of additional components such as glidants, including colloidal silicon dioxide, talc, starch, or tribasic calcium phosphate.

Another solid state property of a pharmaceutical compound that may be important is its dissolution rate in aqueous fluid. The rate of dissolution of an active ingredient in a patient's stomach fluid may have therapeutic consequences since it can impact the rate at which an orally administered active ingredient may reach the patient's bloodstream.

Another solid state property of a pharmaceutical compound that may be important is its thermal behavior, including its melting point. The melting point of the solid form of a drug is optionally high enough to avoid melting or plastic deformation during standard processing operations, as well as concretion of the drug by plastic deformation on storage (See, e.g., Gould, P. L. *Int. J. Pharmaceutics* 1986 33 201-217). It may be desirable in some cases for a solid form to melt above about 100° C. For example, melting point categories used by one pharmaceutical company are, in order of preference, +(mp>120° C.), 0 (mp 80-120° C.), and −(mp<80° C.) (Balbach, S.; Korn, C. *Int. J. Pharmaceutics* 2004 275 1-12).

Active drug molecules may be made into pharmaceutically acceptable salts for therapeutic administration to the patient. Crystalline salts of a drug may offer advantages over the free form of the compound, such as improved solubility, stability, processing improvements, etc., and different crystalline salt forms may offer greater or lesser advantages over one another. However, crystalline salt formation is not predictable, and in fact is not always possible. Moreover, there is no way to predict the properties of a particular crystalline salt of a compound until it is formed. As such, finding the right conditions to obtain a particular crystalline salt form of a compound, with pharmaceutically acceptable properties, can take significant time and effort.

It is also possible to achieve desired properties of a particular API by forming a cocrystal of the API itself, or of a salt of the API. Cocrystals are crystals that contain two or more non-identical molecules. Examples of cocrystals may be found in the Cambridge Structural Database. Examples of cocrystals may also be found at Etter, M. C., and Adsmond, D. A., J. Chem. Soc., Chem. Commun. 1990 589-591; Etter, M. C., MacDonald, J. C., and Bernstein, J., Acta Crystallogr., Sect. B, Struct. Sci. 1990 B46 256-262; and Etter, M. C., Urbańczyk-Lipkowska, Z., Zia-Ebrahimi, M., and Panunto, T. W., J. Am. Chem. Soc. 1990 112 8415-8426, which are incorporated herein by reference in their entireties. The following articles are also incorporated herein by reference in their entireties: Görbotz C. H., and Hersleth, H. P. Acta Cryst. 2000 B56 625-534; and Senthil Kumar, V. S., Nangia, A., Katz, A. K., and Carrell, H. L., Crystal Growth & Design, 2002 2 313-318.

By cocrystallizing an API, or a salt of an API, with a co-former (the other component of the cocrystal), one creates a new solid state form of the API which has unique properties compared with existing solid forms of the API or its salt. For example, a cocrystal may have different dissolution and/or solubility properties than the active agent itself or its salt. Cocrystals containing APIs can be used to deliver APIs therapeutically. New drug formulations comprising cocrystals of APIs with pharmaceutically acceptable co-formers may, in some cases, have superior properties over existing drug formulations. However, cocrystal formation is not predictable, and in fact is not always possible. Moreover, there is no way to predict the properties of a particular cocrystal of a compound until it is formed. As such, finding the right conditions to obtain a particular cocrystal of a compound, with pharmaceutically acceptable properties, can take significant time, effort, and resources.

A crystalline form of a compound, a crystalline salt of the compound, or a cocrystal containing the compound or its salt form generally possesses distinct crystallographic and spectroscopic properties when compared to other crystalline forms having the same chemical composition. Crystallographic and spectroscopic properties of a particular form may be measured by XRPD, single crystal X-ray crystallography, solid state NMR spectroscopy, e.g. $^{13}$C CP/MAS NMR, or Raman spectrometry, among other techniques. A particular crystalline form of a compound, of its salt, or of a cocrystal, often also exhibits distinct thermal behavior. Thermal behavior can be measured in the laboratory by such techniques as, for example, capillary melting point, TGA, and DSC.

In the following description, various aspects and embodiments of the invention will become evident. In its broadest sense, the invention could be practiced without having one or more features of these aspects and embodiments. Further, these aspects and embodiments are exemplary. Additional objects and advantages of the invention will be set forth in part in the description which follows, and in part will be obvious from the description, or may be learned by practicing of the invention. The objects and advantages of the invention will be realized and attained by means of the elements and combinations particularly pointed out in the appended claims.

SUMMARY

In accordance with various embodiments of the invention and after extensive experimentation, the inventors have discovered novel crystalline salt forms of epalrestat, including a potassium anhydrate salt, a sodium anhydrate salt, and a 1-(2-hydroxyethyl)-pyrrolidine anhydrate salt. In accordance with further various embodiments of the invention, the inventors have discovered a novel betaine cocrystal of epalrestat, betaine hydrogen diepalrestat.

The invention in various embodiments also relates to processes of preparing those novel crystalline salts and cocrystal of epalrestat, pharmaceutical compositions containing them, and their use in the treatment and/or prevention of various conditions such as diabetic complications, and also to afford cardioprotection in patients who may be non-diabetic.

As used herein, the term "XRPD" refers to x-ray powder diffraction. The XRPD data disclosed herein were obtained using an Inel XRG-3000 diffractometer equipped with a CPS (Curved Position Sensitive) detector with a 2θ range of 120°. Real time data were collected using Cu—Kα radiation at a resolution of 0.03° 2θ. The tube voltage and amperage were set to 40 kV and 30 mA, respectively. The monochromator slit was set at 5 mm by 160 μm. Samples were prepared for analysis by packing them into thin-walled glass capillaries. Each capillary was mounted onto a goniometer head that is motorized to permit spinning of the capillary during data acquisition. Instrument calibration was performed using a silicon reference standard.

As used herein, the term "DSC" refers to differential scanning calorimetry. DSC data disclosed herein were obtained using a TA Instruments differential scanning calorimeter 2920. The sample was placed into an aluminum DSC pan, and the weight accurately recorded. The pan was crimped with manual pin hole. The sample cell was equilibrated at 25° C. then heated under a nitrogen purge at a rate of 10° C./min, up to a final temperature of 300 or 325° C. Indium metal was used as the calibration standard.

As used herein, the term "$^1$H-NMR" refers to proton nuclear magnetic resonance spectroscopy. Solution $^1$H NMR data disclosed herein were acquired at ambient temperature on a Varian $^{UNITY}$INOVA-400 spectrometer ($^1$H Larmor Frequency=399.8 MHz). The samples were dissolved in NMR-grade dimethyl sulfoxide containing 0.03% TMS. Each $^1$H NMR spectrum represents 40 co-added transients collected with either an 8.1 or 6.01 μsec pulse and a relaxation delay time of 5 seconds. The free induction decay (FID) was exponentially multiplied with a 0.2 Hz Lorentzian line broadening factor to improve the signal-to-noise ratio.

As used herein, the term "TGA" refers to thermogravimetric analysis. TGA data disclosed herein were obtained using a TA Instruments 2950 thermogravimetric analyzer. Each sample was placed in an aluminum sample pan and inserted into the TG furnace. The furnace was first equilibrated at 25° C. and then heated under nitrogen at a rate of 10° C./min, up to a final 1 temperature of 350° C. Nickel and Alumel™ were used as the calibration standards.

As used herein, the term "DVS" refers to dynamic vapor sorption. DVS data disclosed herein were obtained using a VTI SGA-100 Vapor Sorption Analyzer. Sorption and desorption data were collected over a range of 5% to 95% relative humidity ("RH"), at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

As shown herein, solubility data were collected in water at ambient temperature using an orbital shaker. Samples were taken at approximately 1, 3, 6, and 24 hours, and analyzed by UV spectrophotometry using a SpectraMax M2 Microplate Reader. Wavelength calibration and photometric accuracy were performed using the SpectraMax Pro 5 software as an internal calibration of the instrument. The detector was zeroed with a reference well on a microplate filled with water on which data was obtained, and that data was subtracted from collected data. Samples were analyzed in the UV range at room temperature in the wells of a 96-well quartz plate.

As used herein with respect to the various analytical techniques described herein and data generated therefrom, the term "substantially" the same as or similar to is meant to convey that a particular set of analytical data is, within acceptable scientific limits, sufficiently similar to that disclosed herein such that one of skill in the art would appreciate that the crystal salt form of the compound is the same as that of the present invention. One of skill in the art would appreciate that certain analytical techniques, such as XRPD, $^1$H-NMR, DSC, TGA, DVS, and UV spectrophotometry will not produce exactly the same results every time due to, for example, instrumental variation, sample preparation, scientific error, etc. By way of example only, XRPD results (i.e. peak locations, intensities, and/or presence) may vary slightly from sample to sample, despite the fact that the samples are, within accepted scientific principles, the same form, and this may be due to, for example, preferred orientation or varying solvent or water content. It is well within the ability of those skilled in the art, looking at the data as a whole, to appreciate whether such differences indicate a different form, and thus determine whether analytical data being compared to those disclosed herein are substantially similar. In this regard, and as is commonly practiced within the scientific community, it is not intended that the exemplary analytical data of the novel salts of epalrestat disclosed herein be met literally in order to determine whether comparative data represent the same form as those disclosed and claimed herein, such as, for example, whether each and every peak of an exemplary XRPD pattern of a novel salt or cocrystal of epalrestat disclosed herein is present in the comparative data, in the same location, and/or of the same intensity. Rather, as discussed above, it is intended that those of skill in the art, using accepted scientific principles, will make a determination based on the data as a whole regarding whether comparative analytical data represent the same or a different form of any of the novel crystalline salts of epalrestat or the novel betaine hydrogen diepalrestat cocrystal disclosed herein.

As used herein, "hep" means hydroxyethylpyrrolidone.

As used herein, the terms "betaine hydrogen diepalrestat" and "betaine hydrogen diacid cocrystal of epalrestat," including variations which use the chemical name "5-[(1Z,2E)-2-methyl-3-phenylpropenylidene]-4-oxo-2-thioxo-3-thiazolidineacetic acid" in place of the common name "epalrestat," are used interchangeably to refer to the novel betaine cocrystal of epalrestat described herein.

It is to be understood that both the foregoing general description and the following detailed description are exemplary and explanatory only and are not restrictive of the invention, as claimed.

BRIEF DESCRIPTION OF THE FIGURES

FIG. 11D is an ¹H-NMR spectrum from 3.0 to 1.4 ppm of a crystalline 1-(2-hydroxyethyl)-pyrrolidine anhydrate salt of epalrestat, according to one embodiment of the invention;

FIG. 16 is a TGA profile of a betaine hydrogen diacid cocrystal of epalrestat, according to one embodiment of the invention; and.

DESCRIPTION OF EXEMPLARY EMBODIMENTS

One aspect of the invention described herein relates to novel crystalline salt forms of epalrestat. Specifically, the novel crystalline salts which have been discovered include a potassium anhydrate salt, a sodium anhydrate salt, and a 1-(2-hydroxyethyl)-pyrrolidine anhydrate salt of epalrestat. Exemplary methods of preparation of the novel crystalline salt forms of epalrestat according to various embodiments of the invention are described below in the examples.

All of the inventive salts of epalrestat as described herein can be obtained in a crystalline solid form. The salts of the invention are described as crystalline because of the high degree of crystallinity of the forms as depicted by the XRPD patterns provided in FIGS. 1-3. The forms are shown to have distinct physicochemical properties. The novel crystalline salt forms of epalrestat according to various embodiments of the invention are particularly suitable for the preparation of stable pharmaceutical preparations.

Figure 1:
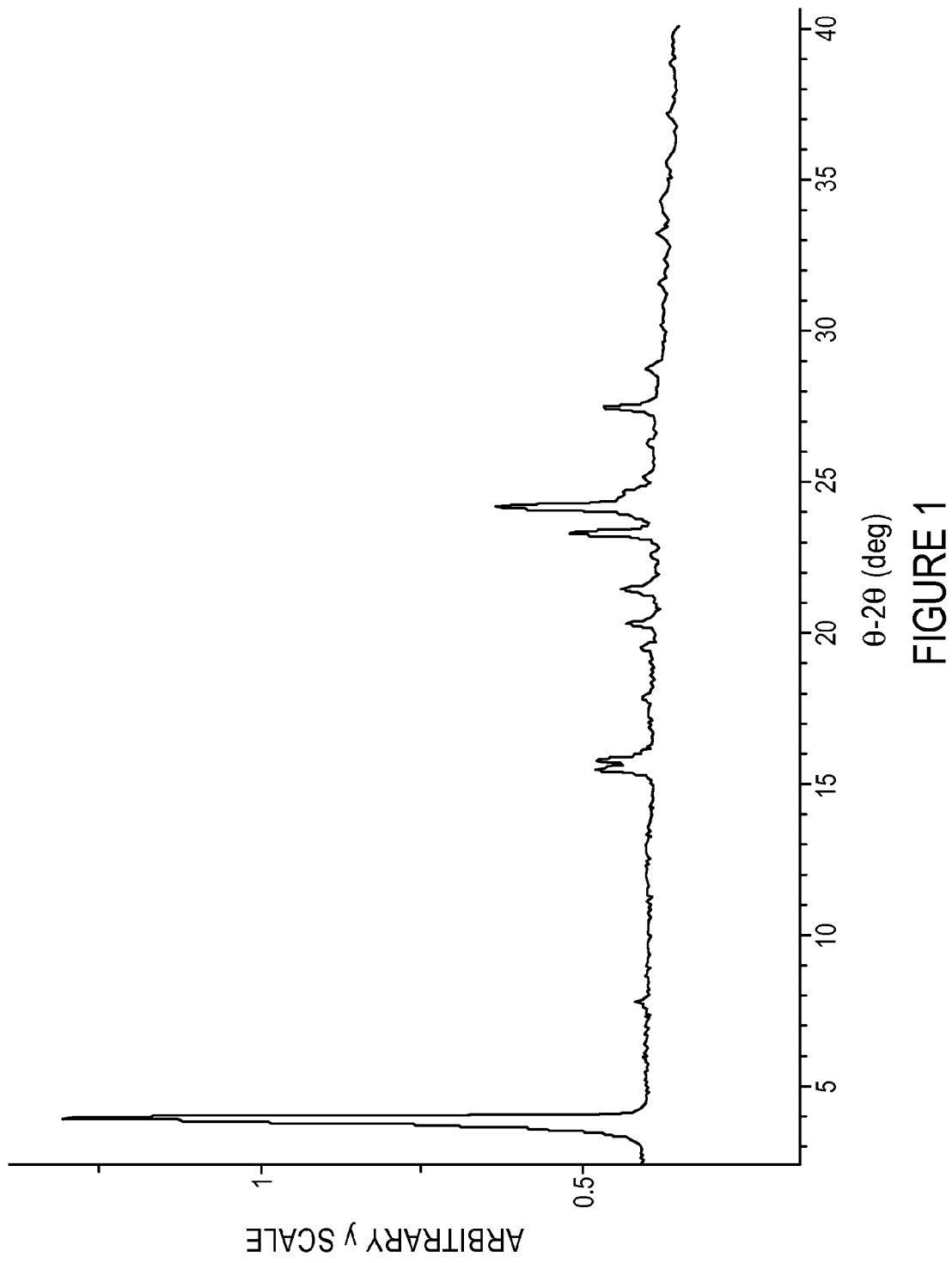
FIG. 1 is an XRPD pattern of a crystalline potassium anhydrate salt of epalrestat, according to one embodiment of the invention.
Figure 5:
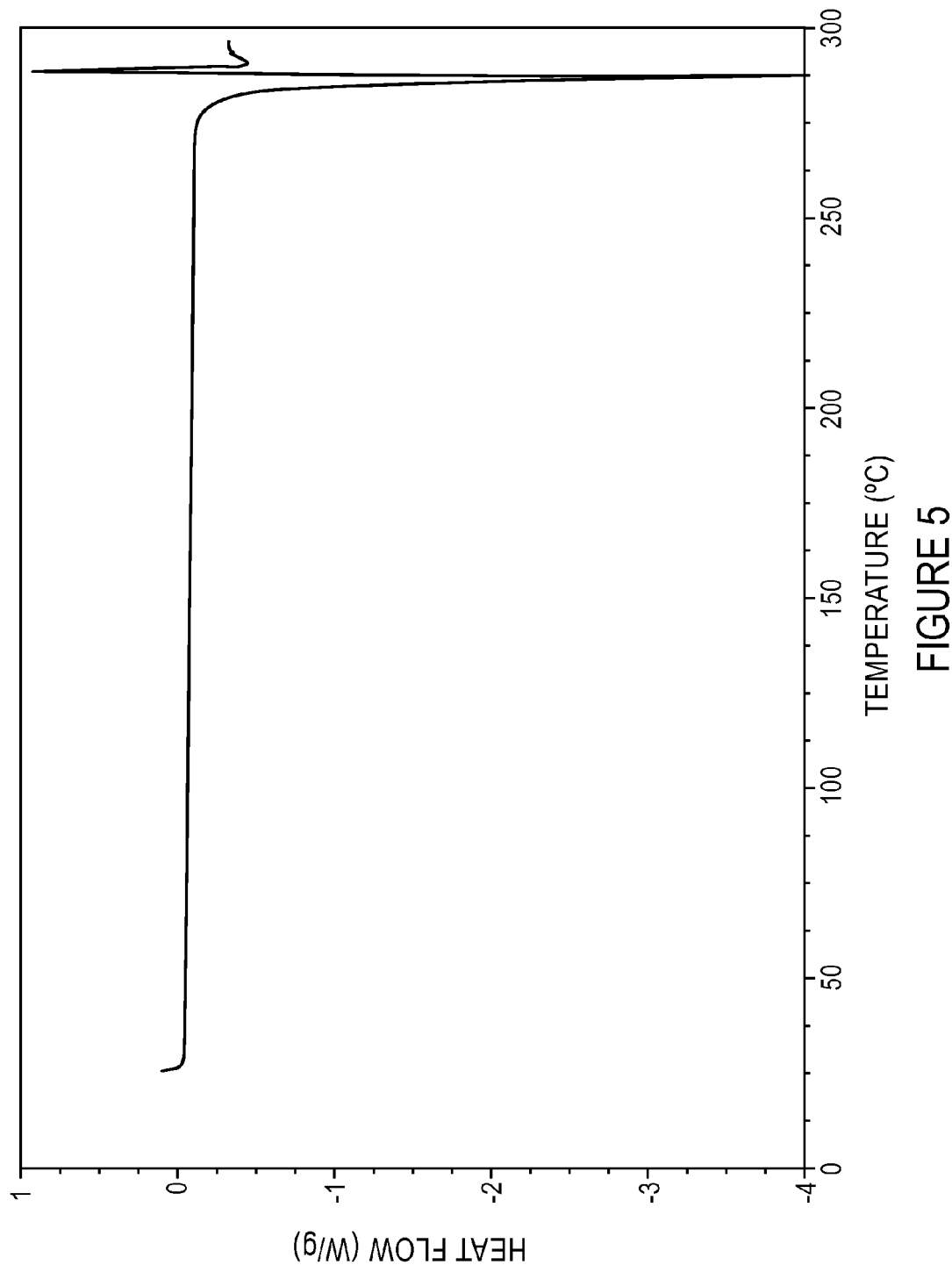
FIG. 5 is a DSC thermogram of a crystalline potassium anhydrate salt of epalrestat, according to one embodiment of the invention.
Figure 13:
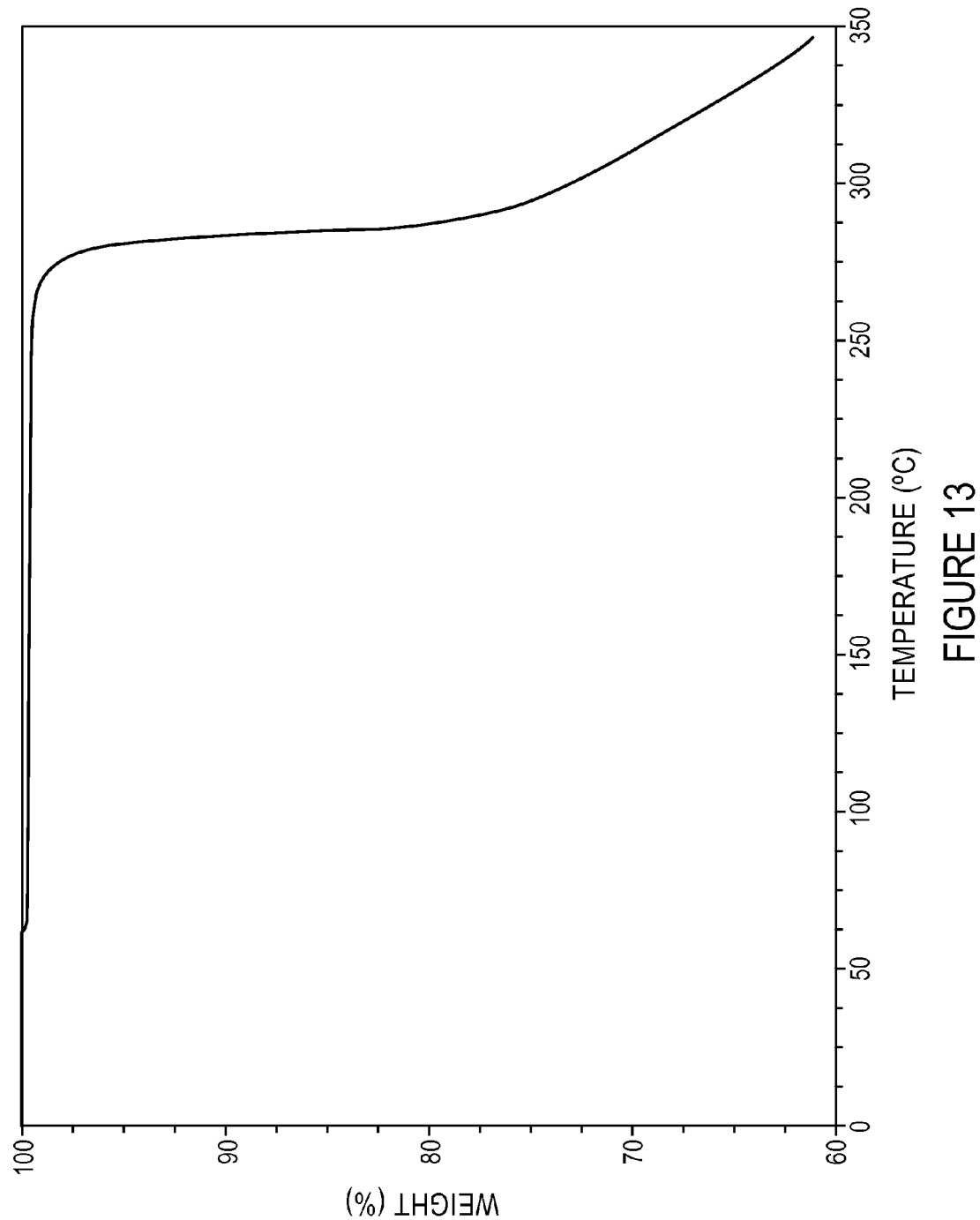
FIG. 13 is a TGA profile of a crystalline potassium anhydrate salt of epalrestat, according to one embodiment of the invention.

The crystalline potassium anhydrate salt of epalrestat is characterized by an XRPD pattern substantially as shown in FIG. 1, a DSC thermogram substantially as shown in FIG. 5, ¹H-NMR spectra substantially as shown in FIGS. 9A-9D, and a TGA profile substantially as shown in FIG. 13. An exemplary listing of representative XRPD peaks of a crystalline potassium anhydrate salt of epalrestat according to the invention can be found in Table 1. Prominent XRPD peaks may include, in one exemplary embodiment, peaks at 3.8, 15.4, and 15.7 °2θ±0.2. An exemplary listing of representative NMR data can be found in Table 2.

TABLE 1

| °2θ | d space (Å) | Intensity (%) |
| --- | --- | --- |
| 3.8 ± 0.2 | 22.95 ± 1.22 | 100 |
| 7.8 ± 0.2 | 11.36 ± 0.30 | 3 |
| 15.4 ± 0.2 | 5.74 ± 0.07 | 11 |
| 15.7 ± 0.2 | 5.63 ± 0.07 | 11 |
| 17.8 ± 0.2 | 4.98 ± 0.06 | 2 |
| 19.4 ± 0.2 | 4.56 ± 0.05 | 3 |
| 20.2 ± 0.2 | 4.39 ± 0.04 | 6 |
| 21.4 ± 0.2 | 4.15 ± 0.04 | 7 |
| 22.6 ± 0.2 | 3.94 ± 0.03 | 2 |
| 23.3 ± 0.2 | 3.82 ± 0.03 | 17 |
| 24.1 ± 0.2 | 3.69 ± 0.03 | 31 |
| 25.2 ± 0.2 | 3.54 ± 0.03 | 3 |
| 26.3 ± 0.2 | 3.39 ± 0.03 | 3 |
| 27.5 ± 0.2 | 3.25 ± 0.02 | 11 |
| 28.8 ± 0.2 | 3.11 ± 0.02 | 3 |

TABLE 2

| protons | peak position (ppm) | multiplicity | coupling constant (Hz) | number of protons |
| --- | --- | --- | --- | --- |
| $CH_3$ | 2.21 | doublet | 1 | 3 |
| $CH_2$ | 4.24 | singlet | — | 2 |
| olefin/aromatic | 7.32 | broad singlet | — | 1 |
| olefin/aromatic | 7.35-7.39 | multiplet | — | 1 |
| olefin/aromatic | 7.42-7.49 | multiplet | — | 4 |
| olefin | 7.51 | doublet | 1 | 1 |

Figure 2:
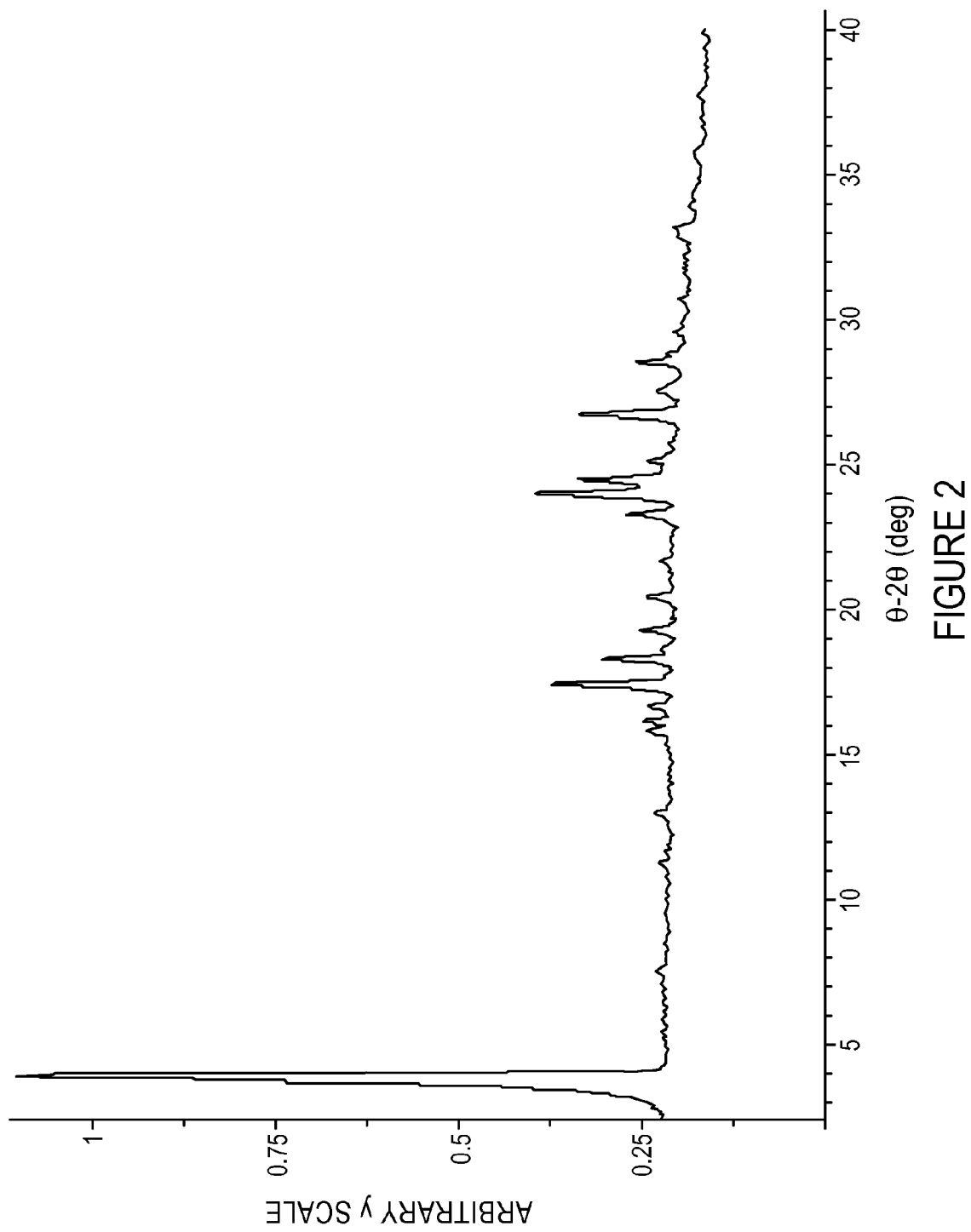
FIG. 2 is an XRPD pattern of a crystalline sodium anhydrate salt of epalrestat, according to one embodiment of the invention.
Figure 6:
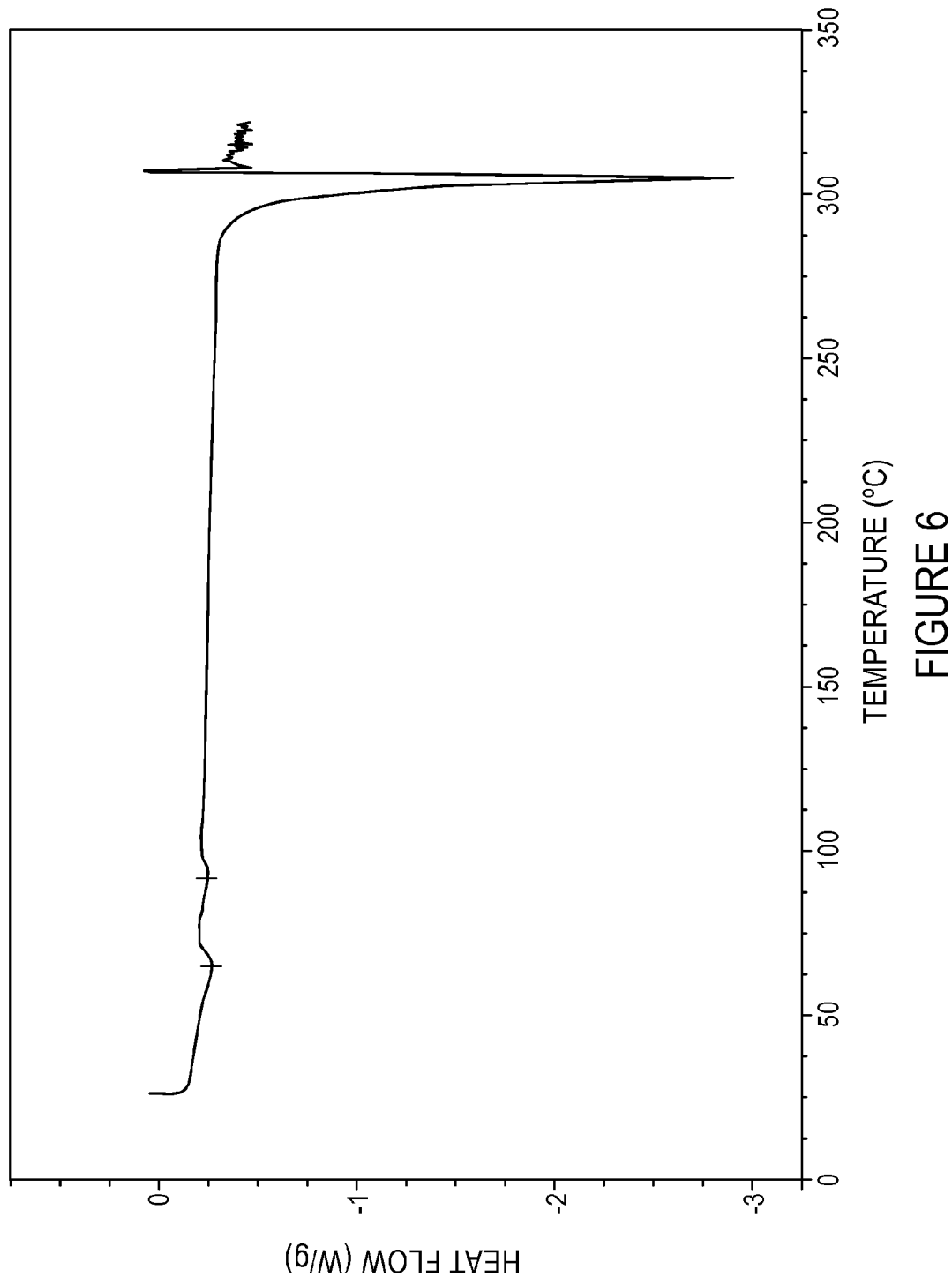
FIG. 6 is a DSC thermogram of a crystalline sodium anhydrate salt of epalrestat, according to one embodiment of the invention.
Figure 14:
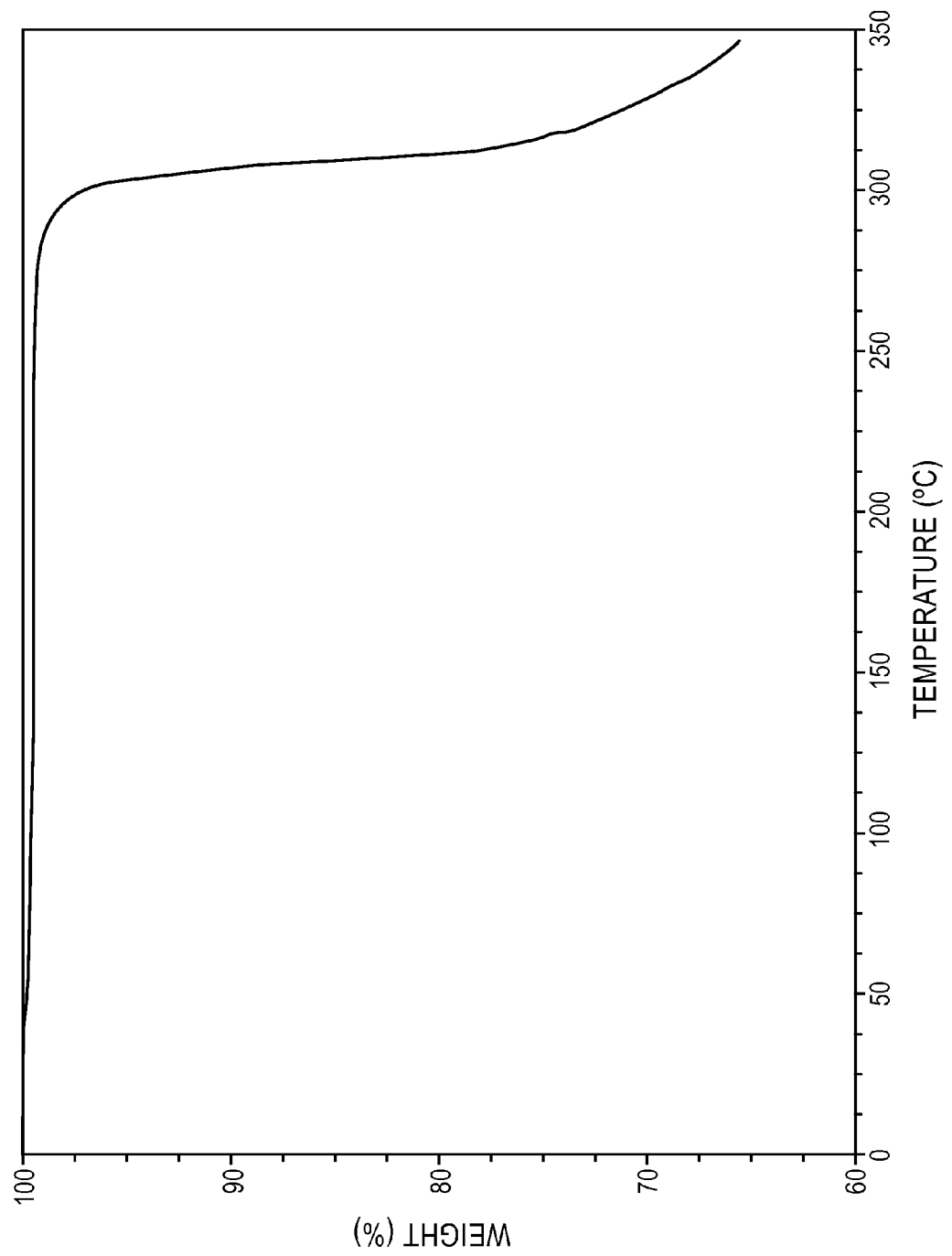
FIG. 14 is a TGA profile of a crystalline sodium anhydrate salt of epalrestat, according to one embodiment of the invention.

The crystalline sodium anhydrate salt of epalrestat is characterized by an XRPD pattern substantially as shown in FIG. 2, a DSC thermogram substantially as shown in FIG. 6, ¹H-NMR spectra substantially as shown in FIGS. 10A-10D, and a TGA profile substantially as shown in FIG. 14. An exemplary listing of representative XRPD peaks of a crystalline sodium anhydrate salt of epalrestat according to the invention can be found in Table 3. Prominent XRPD peaks may include, in one exemplary embodiment, peaks at 3.7, 17.3, and 18.2 °2θ±0.2. An exemplary listing of representative NMR data can be found in Table 4.

TABLE 3

| °2θ | d space (Å) | Intensity (%) |
| --- | --- | --- |
| 3.7 ± 0.2 | 24.08 ± 1.35 | 100 |
| 7.4 ± 0.2 | 11.91 ± 0.33 | 2 |
| 11.2 ± 0.2 | 7.90 ± 0.14 | 2 |
| 12.9 ± 0.2 | 6.86 ± 0.11 | 3 |
| 15.7 ± 0.2 | 5.63 ± 0.07 | 5 |
| 16.1 ± 0.2 | 5.52 ± 0.07 | 5 |
| 16.6 ± 0.2 | 5.34 ± 0.06 | 5 |
| 17.3 ± 0.2 | 5.12 ± 0.06 | 21 |
| 18.2 ± 0.2 | 4.88 ± 0.05 | 12 |
| 18.5 ± 0.2 | 4.79 ± 0.05 | 2 |
| 19.2 ± 0.2 | 4.61 ± 0.05 | 6 |
| 20.4 ± 0.2 | 4.36 ± 0.04 | 5 |
| 21.6 ± 0.2 | 4.11 ± 0.04 | 3 |
| 23.2 ± 0.2 | 3.83 ± 0.03 | 8 |
| 23.9 ± 0.2 | 3.72 ± 0.03 | 25 |
| 24.4 ± 0.2 | 3.65 ± 0.03 | 17 |
| 25.1 ± 0.2 | 3.55 ± 0.03 | 5 |

TABLE 3-continued

| °2θ | d space (Å) | Intensity (%) |
|---|---|---|
| 25.7 ± 0.2 | 3.47 ± 0.03 | 2 |
| 26.6 ± 0.2 | 3.35 ± 0.02 | 17 |
| 27.5 ± 0.2 | 3.25 ± 0.02 | 4 |
| 28.5 ± 0.2 | 3.13 ± 0.02 | 8 |
| 28.8 ± 0.2 | 3.10 ± 0.02 | 3 |
| 29.5 ± 0.2 | 3.03 ± 0.02 | 2 |

TABLE 4

| protons | peak position (ppm) | multiplicity | coupling constant (Hz) | number of protons |
|---|---|---|---|---|
| $CH_3$ | 2.21 | doublet | 1 | 3 |
| $CH_2$ | 4.27 | singlet | — | 2 |
| olefin/aromatic | 7.29-7.34 | multiplet | — | 1 |
| olefin/aromatic | 7.35-7.41 | multiplet | — | 1 |
| olefin/aromatic | 7.42-7.49 | multiplet | — | 4 |

Figure 3:
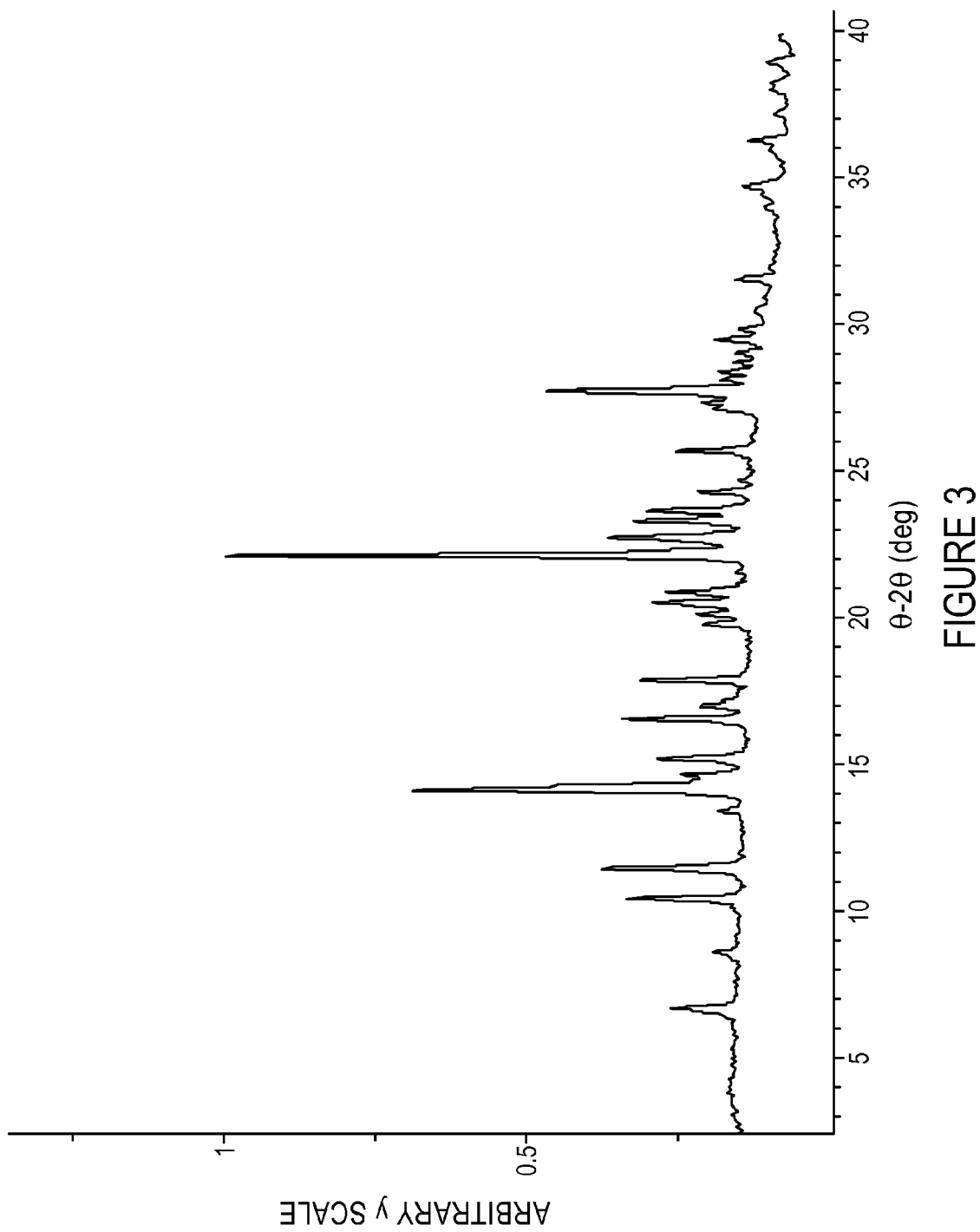
FIG. 3 is an XRPD pattern of a crystalline 1-(2-hydroxyethyl)-pyrrolidine anhydrate salt of epalrestat, according to one embodiment of the invention.
Figure 7:
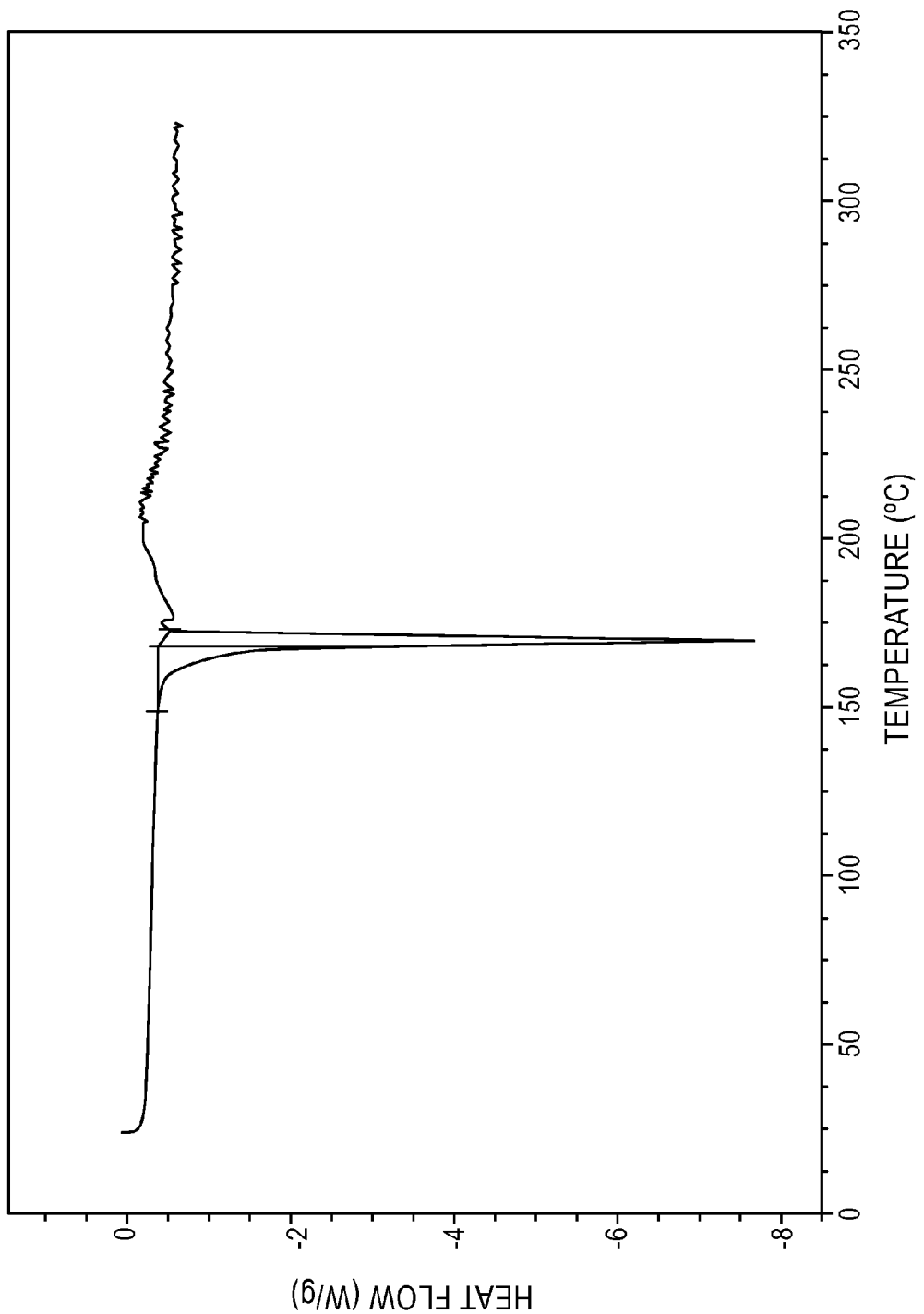
FIG. 7 is a DSC thermogram of a crystalline 1-(2-hydroxyethyl)-pyrrolidine anhydrate salt of epalrestat, according to one embodiment of the invention.
Figure 15:
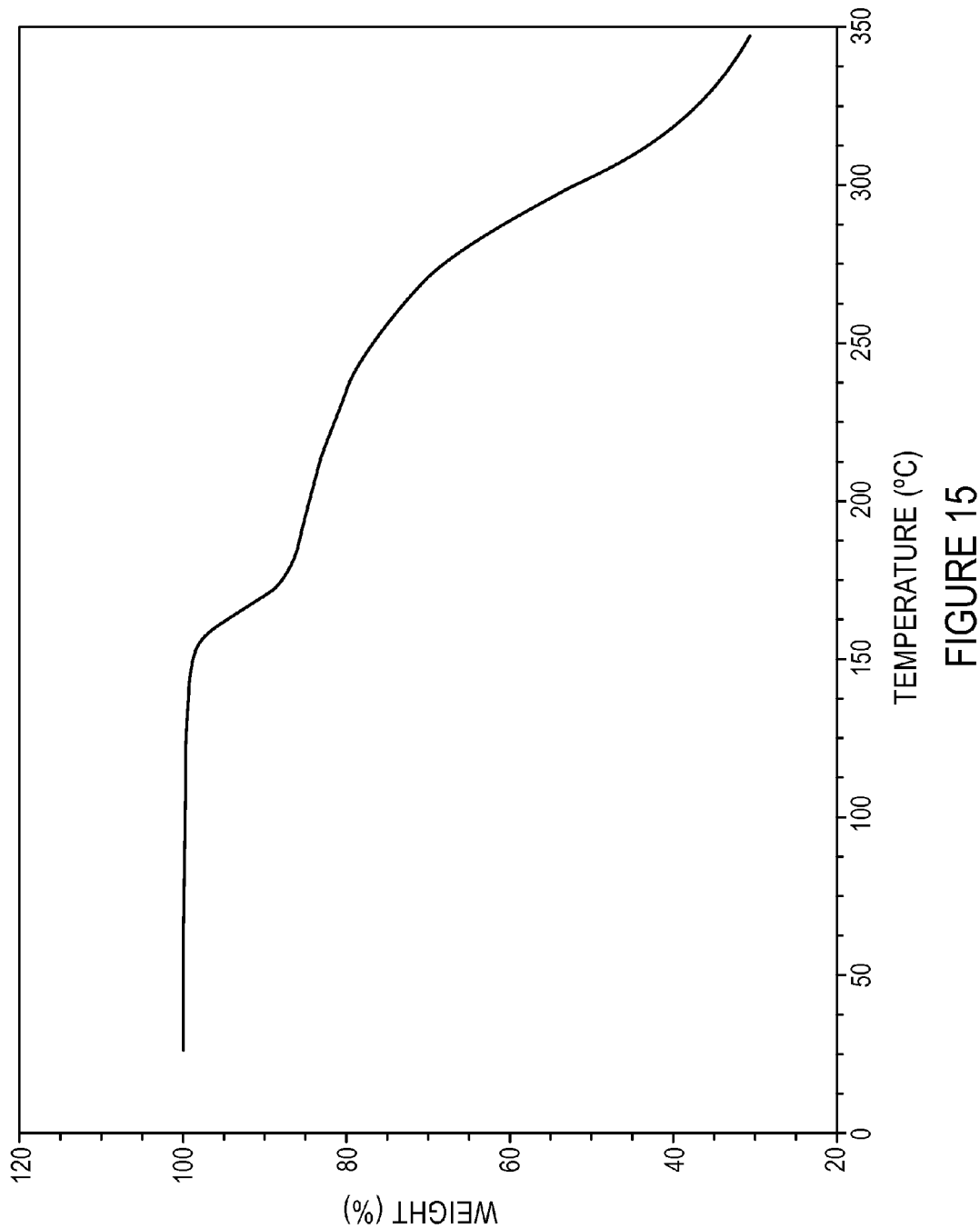
FIG. 15 is a TGA profile of a crystalline 1-(2-hydroxyethyl)-pyrrolidine anhydrate salt of epalrestat, according to one embodiment of the invention.

The crystalline 1-(2-hydroxyethyl)-pyrrolidine anhydrate salt of epalrestat is characterized by an XRPD pattern substantially as shown in FIG. 3, a DSC thermogram substantially as shown in FIG. 7, $^1$H-NMR spectra substantially as shown in FIGS. 11A-11D, and a TGA profile substantially as shown in FIG. 15. An exemplary listing of representative XRPD peaks of a crystalline 1-(2-hydroxyethyl)-pyrrolidine anhydrate salt of epalrestat according to the invention can be found in Table 5. Prominent XRPD peaks may include, in one exemplary embodiment, peaks at 6.7, 10.5, 11.5, and 14.2 °2θ±0.2. An exemplary listing of representative NMR data can be found in Table 6.

TABLE 5

| °2θ | d space (Å) | Intensity (%) |
|---|---|---|
| 6.7 ± 0.2 | 13.13 ± 0.40 | 13 |
| 8.6 ± 0.2 | 10.22 ± 0.24 | 5 |
| 10.5 ± 0.2 | 8.44 ± 0.16 | 22 |
| 11.5 ± 0.2 | 7.70 ± 0.13 | 27 |
| 13.4 ± 0.2 | 6.58 ± 0.10 | 5 |
| 14.2 ± 0.2 | 6.24 ± 0.09 | 64 |
| 14.7 ± 0.2 | 6.02 ± 0.08 | 13 |
| 15.2 ± 0.2 | 5.81 ± 0.08 | 17 |
| 16.6 ± 0.2 | 5.34 ± 0.06 | 23 |
| 17.0 ± 0.2 | 5.20 ± 0.06 | 9 |
| 18.0 ± 0.2 | 4.94 ± 0.05 | 21 |
| 19.9 ± 0.2 | 4.47 ± 0.04 | 9 |
| 20.2 ± 0.2 | 4.39 ± 0.04 | 10 |
| 20.6 ± 0.2 | 4.31 ± 0.04 | 19 |
| 21.0 ± 0.2 | 4.24 ± 0.04 | 15 |
| 22.3 ± 0.2 | 3.99 ± 0.04 | 100 |
| 22.8 ± 0.2 | 3.89 ± 0.03 | 27 |
| 23.4 ± 0.2 | 3.80 ± 0.03 | 22 |
| 23.8 ± 0.2 | 3.74 ± 0.03 | 20 |
| 24.4 ± 0.2 | 3.64 ± 0.03 | 10 |
| 24.8 ± 0.2 | 3.58 ± 0.03 | 3 |
| 25.8 ± 0.2 | 3.45 ± 0.03 | 15 |
| 27.5 ± 0.2 | 3.25 ± 0.02 | 11 |
| 27.9 ± 0.2 | 3.20 ± 0.02 | 41 |
| 28.3 ± 0.2 | 3.15 ± 0.02 | 8 |
| 28.6 ± 0.2 | 3.12 ± 0.02 | 8 |
| 28.9 ± 0.2 | 3.09 ± 0.02 | 6 |
| 29.2 ± 0.2 | 3.06 ± 0.02 | 5 |
| 29.6 ± 0.2 | 3.01 ± 0.02 | 10 |

TABLE 6

| protons | peak position (ppm) | multiplicity | coupling constant (Hz) | number of protons |
|---|---|---|---|---|
| $CH_2$ (hep) | 1.79-1.86 | multiplet | — | 41.03 (4) |
| $CH_3$ | 2.22 | doublet | 1 | 30.32 (3) |
| $CH_2$ (hep) | 2.97-3.03 | multiplet | — | 61.72 (6) |
| $CH_2$ (hep) | 3.62 | triplet | 5 | 20.95 (2) |
| $CH_2$ | 4.45 | singlet | — | 20.36 (2) |
| olefin/aromatic | 7.35-7.39 | multiplet | — | 20.66 (2) |
| olefin/aromatic | 7.43-7.49 | multiplet | — | 40.69 (4) |
| olefin | 7.56 | doublet | 1 | 10.00 (1) |

A further aspect of the invention described herein relates to a novel betaine cocrystal of epalrestat. Specifically, the novel cocrystal which has been discovered is a betaine hydrogen diacid cocrystal of epalrestat having approximately two moles of epalrestat and approximately one mole of betaine. In one embodiment, the novel cocrystal is anhydrous. Exemplary methods of preparation of the novel betaine cocrystal of epalrestat according to the invention are described below in the examples.

Figure 4:
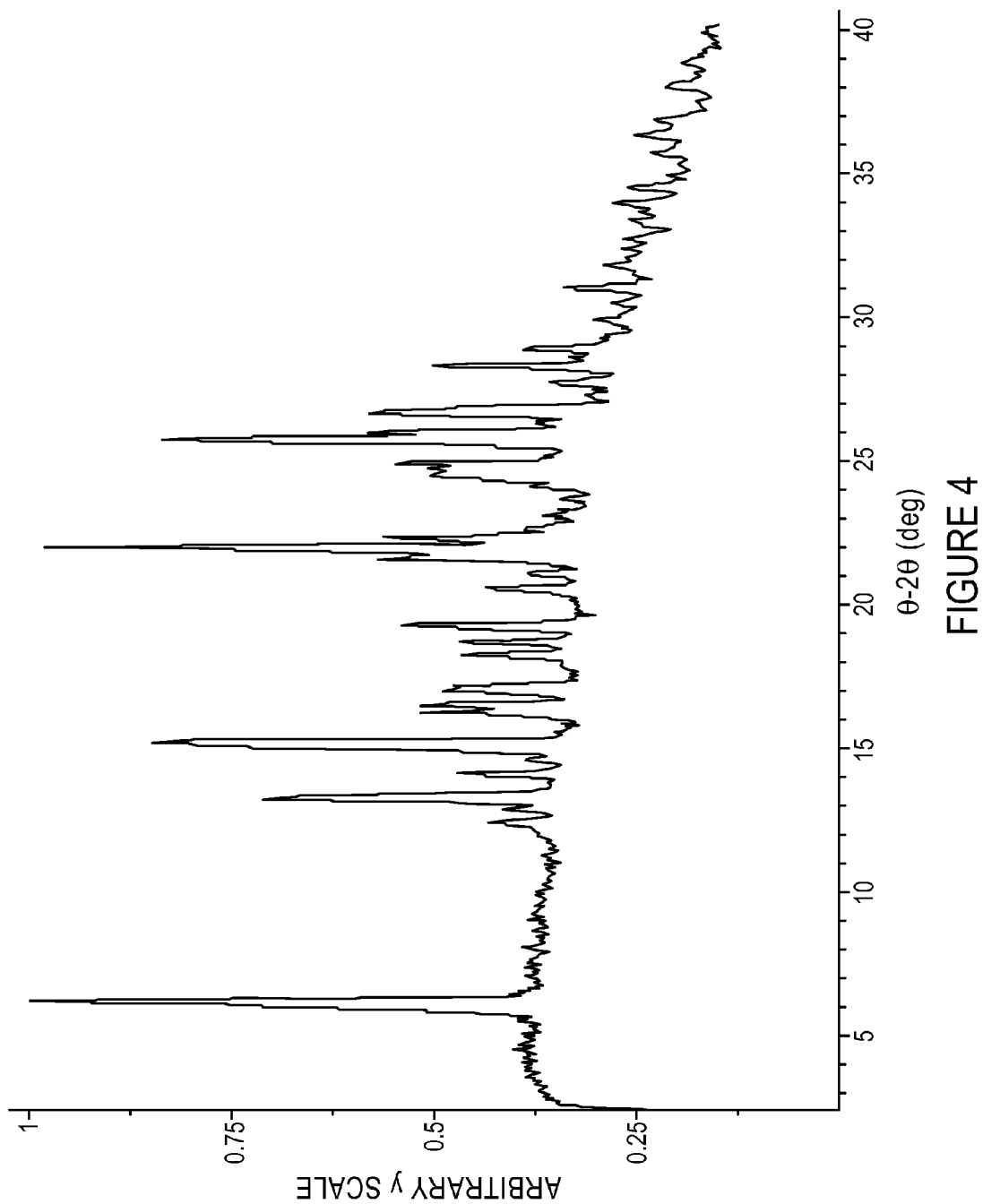
FIG. 4 is an XRPD pattern of a betaine hydrogen diacid cocrystal of epalrestat, according to one embodiment of the invention.

The novel cocrystal described herein is obtained in a crystalline solid form, as seen by the high degree of crystallinity depicted in the XRPD pattern provided in FIG. 4. The cocrystal is shown to have distinct physicochemical properties and is stable to decomposition from uptake of moisture at specified conditions. The cocrystal of epalrestat described herein is particularly suitable for the preparation of stable pharmaceutical preparations.

Figure 8:
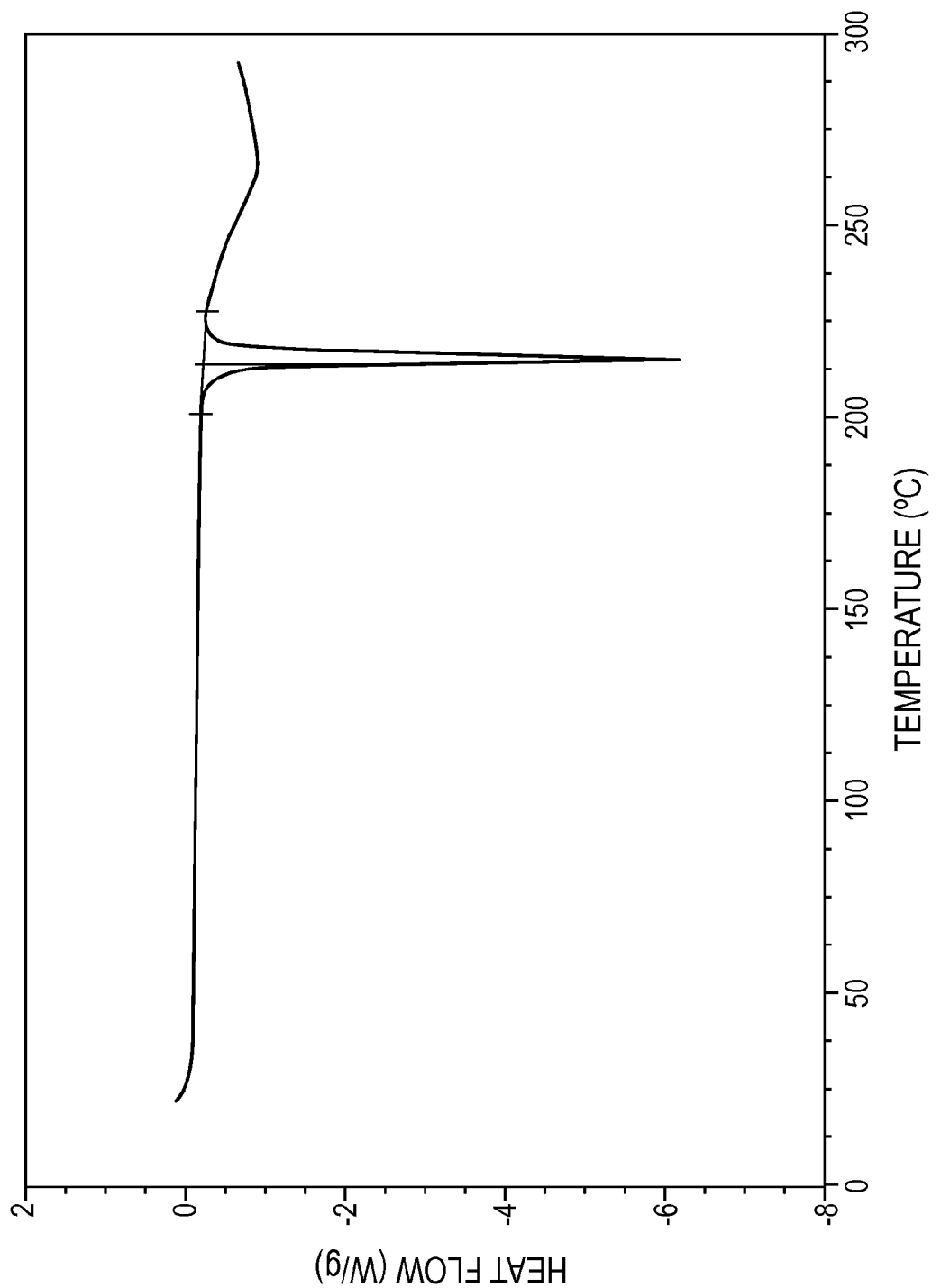
FIG. 8 is a DSC thermogram of a betaine hydrogen diacid cocrystal of epalrestat, according to one embodiment of the invention.
Figure 9A:
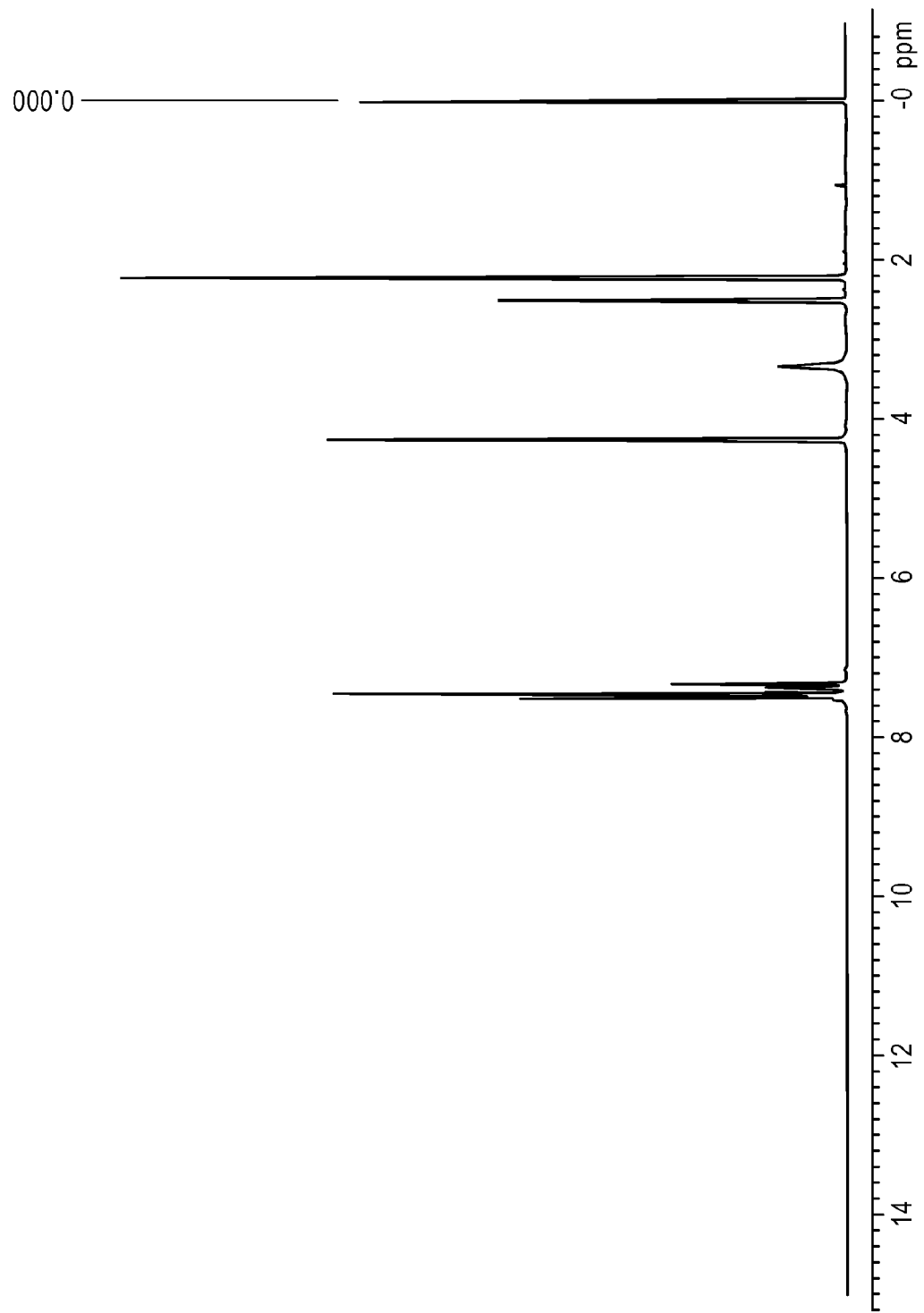
FIG. 9A is a full $^1$H-NMR spectrum of a crystalline potassium anhydrate salt of epalrestat, according to one embodiment of the invention.
Figure 9B:
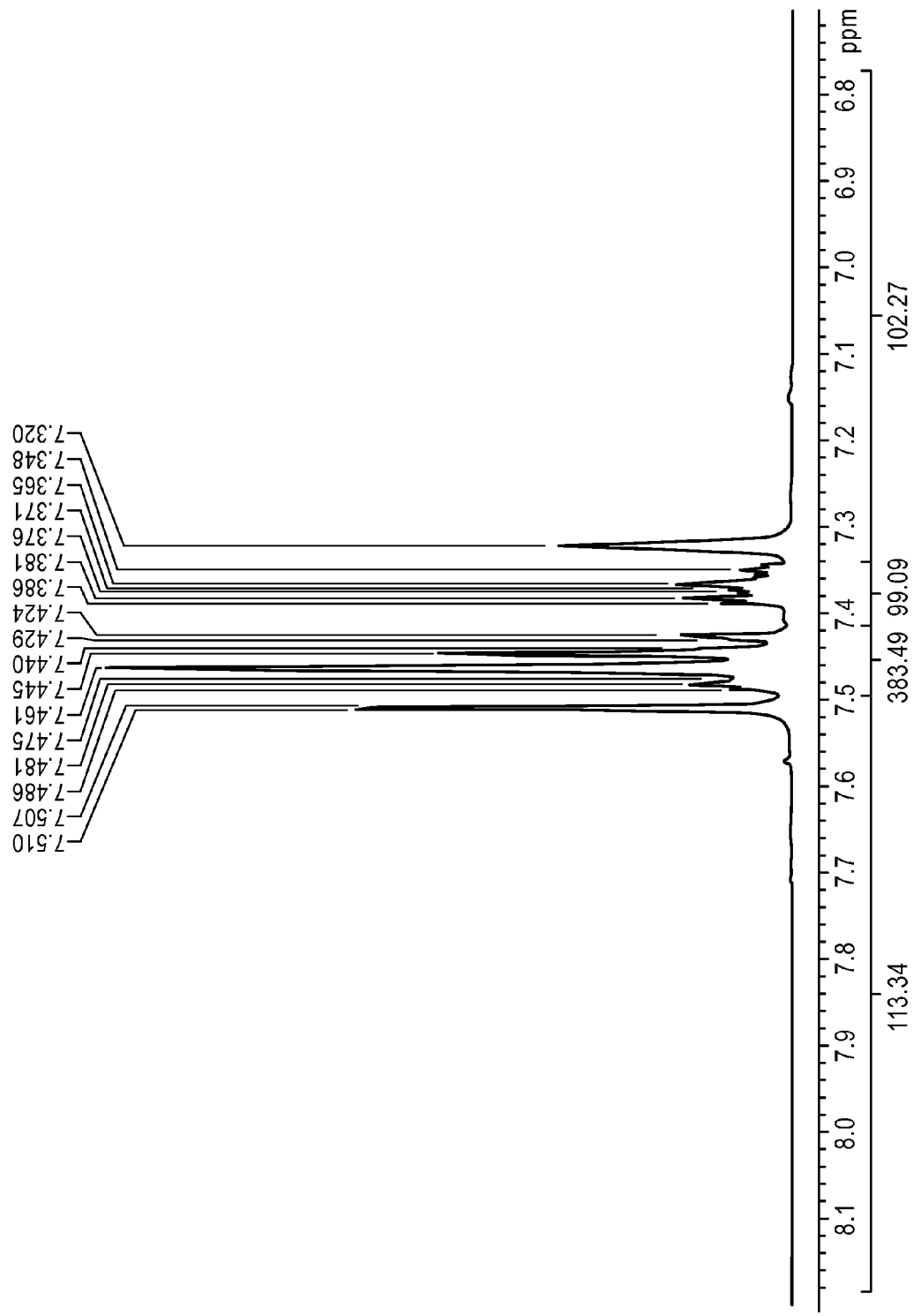
FIG. 9B is an $^1$H-NMR spectrum from 8.1 to 6.8 ppm of a crystalline potassium anhydrate salt of epalrestat, according to one embodiment of the invention.
Figure 9C:
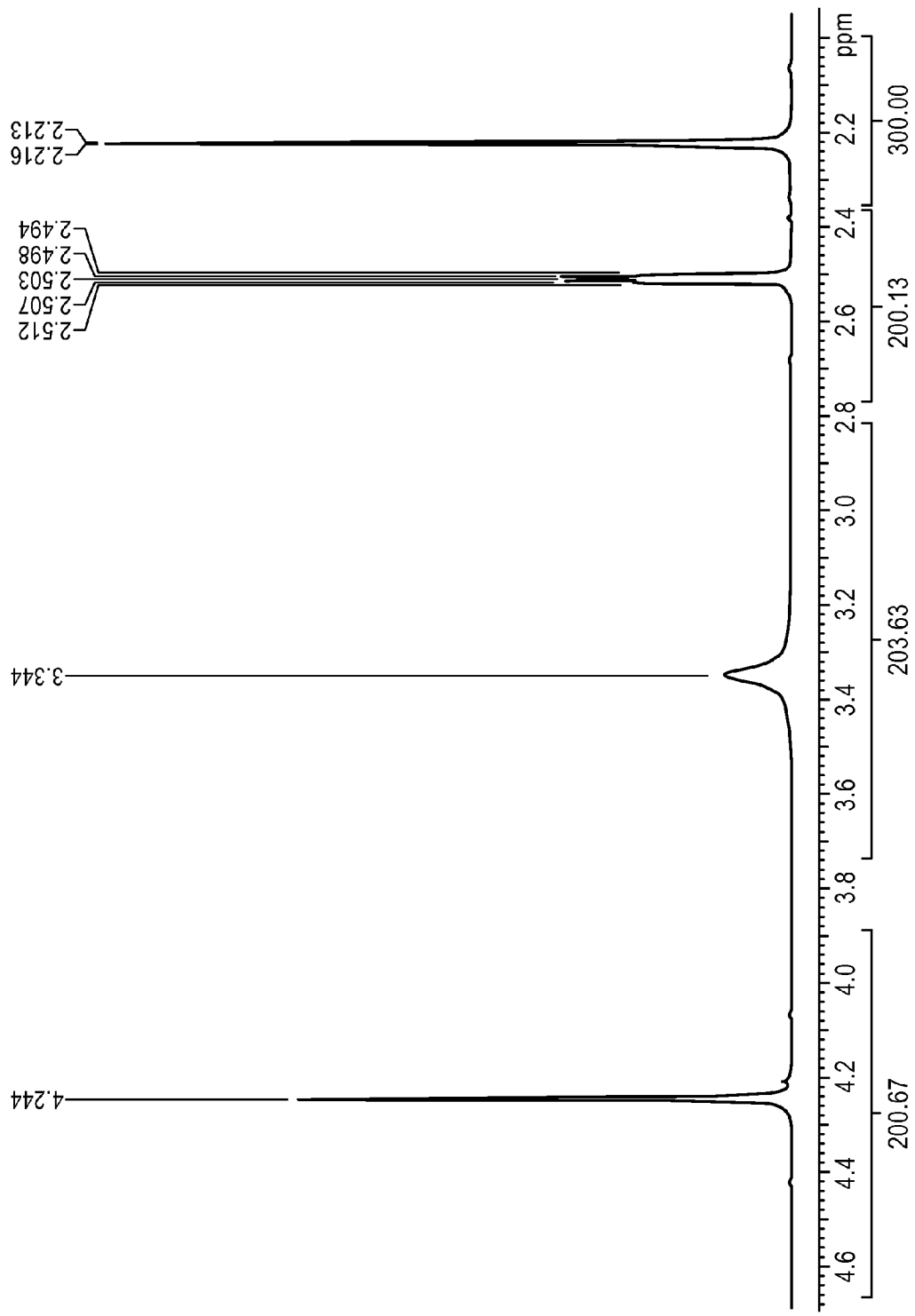
FIG. 9C is an $^1$H-NMR spectrum from 4.6 to 2.1 ppm of a crystalline potassium anhydrate salt of epalrestat, according to one embodiment of the invention.
Figure 9D:
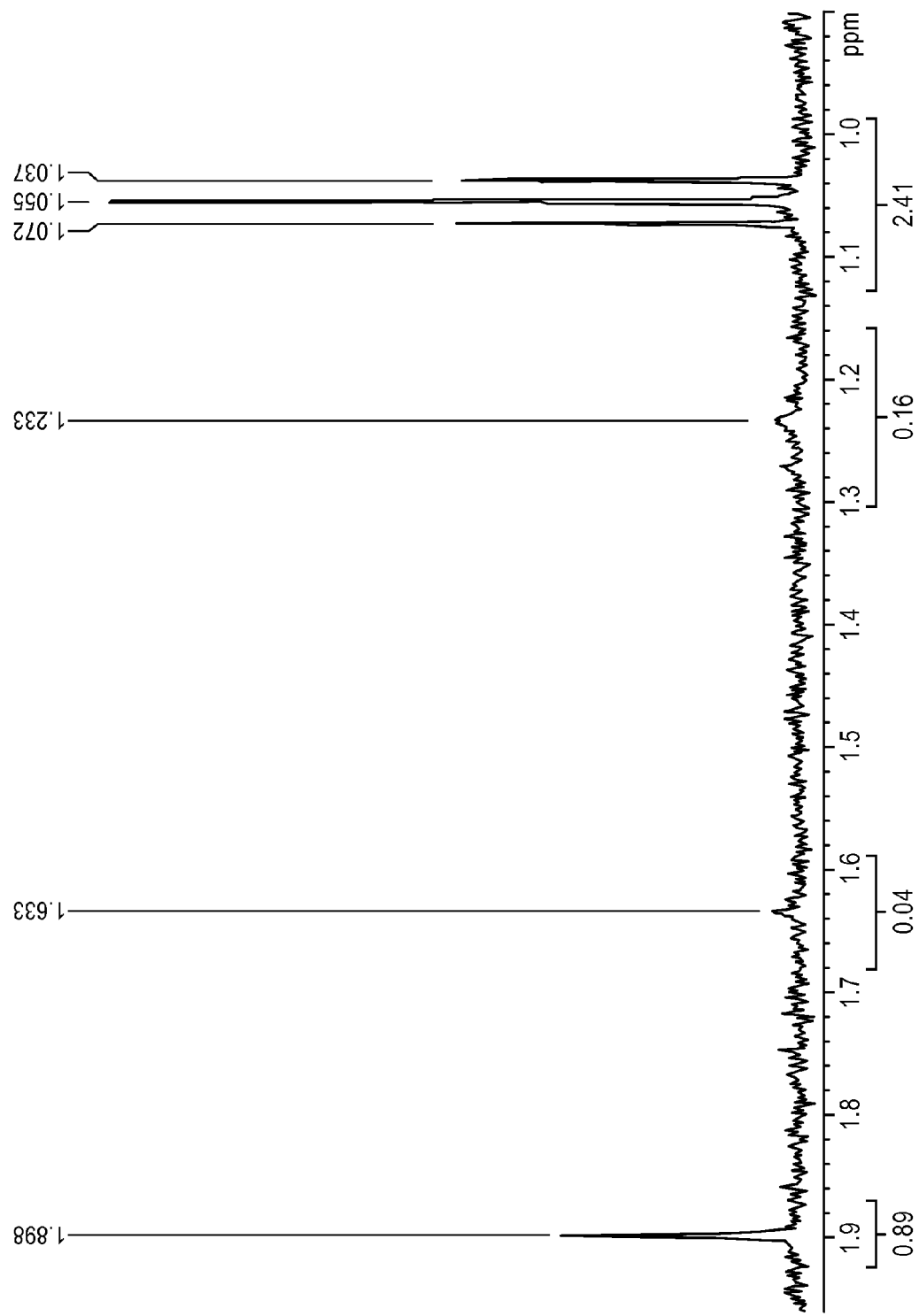
FIG. 9D is an $^1$H-NMR spectrum from 1.9 to 1.0 ppm of a crystalline potassium anhydrate salt of epalrestat, according to one embodiment of the invention.
Figure 10A:
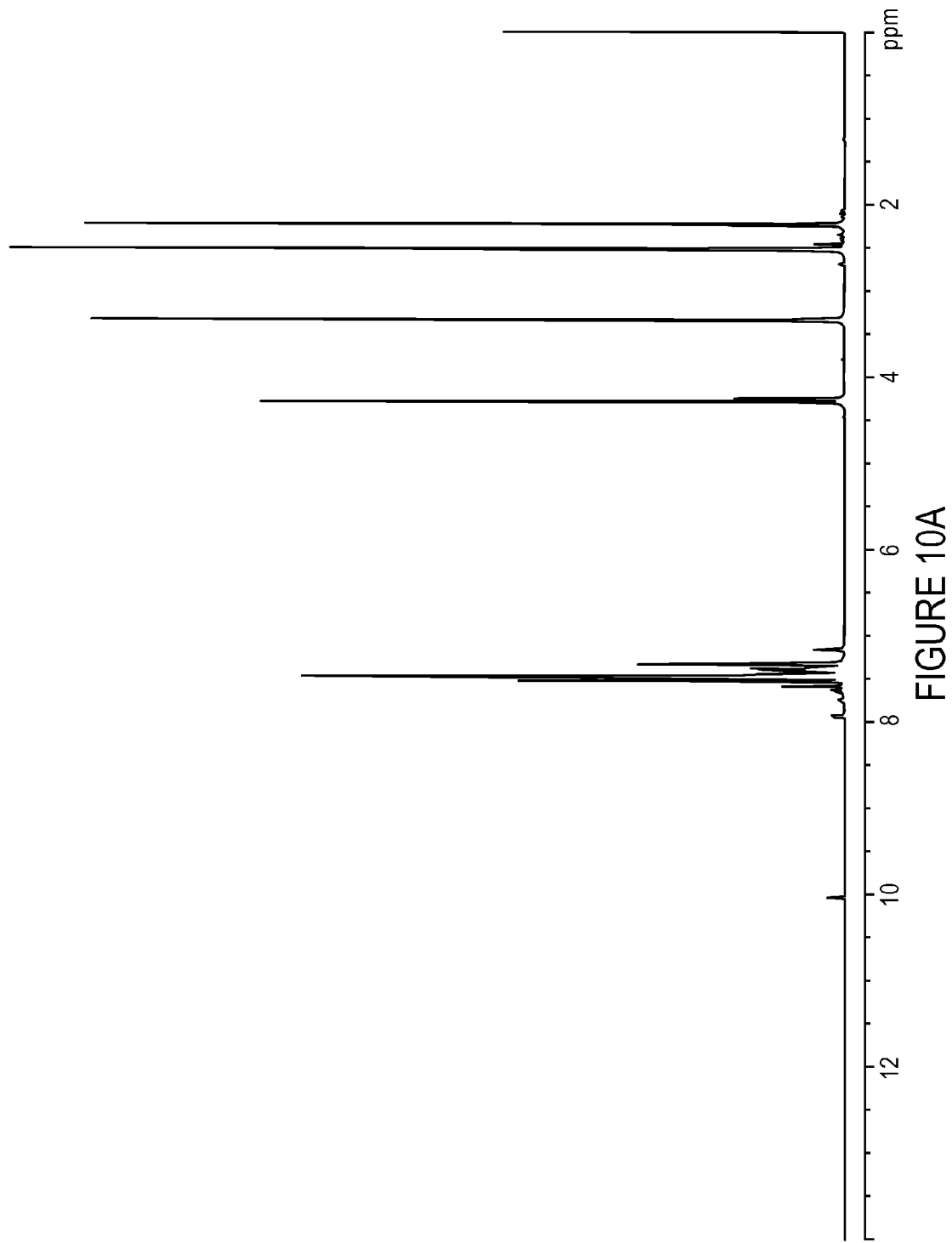
FIG. 10A is a full $^1$H-NMR spectrum of a crystalline sodium anhydrate salt of epalrestat, according to one embodiment of the invention.
Figure 10B:
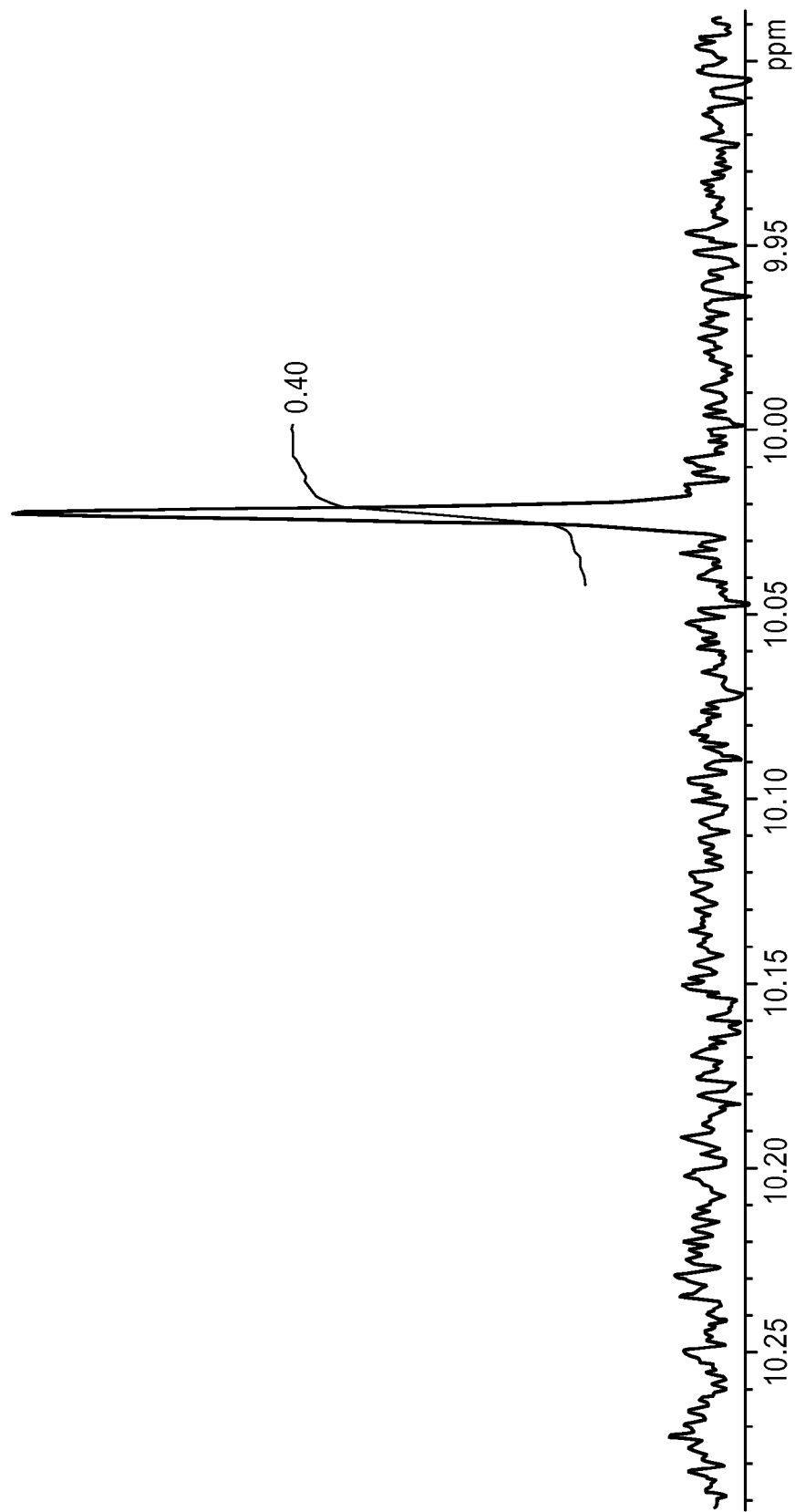
FIG. 10B is an $^1$H-NMR spectrum from 10.25 to 9.95 ppm of a crystalline sodium anhydrate salt of epalrestat, according to one embodiment of the invention.
Figure 10C:
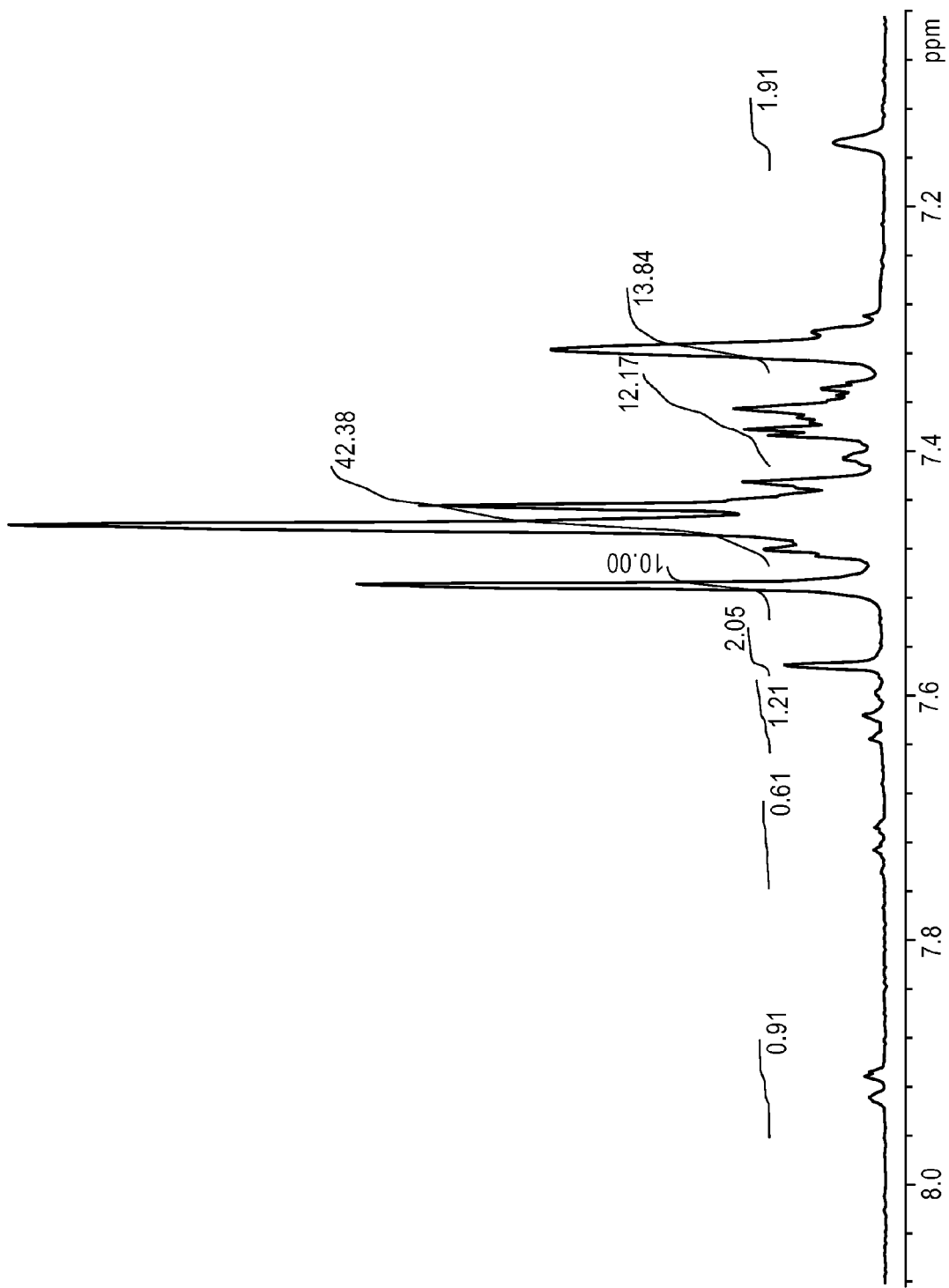
FIG. 10C is an $^1$H-NMR spectrum from 8.0 to 7.14 ppm of a crystalline sodium anhydrate salt of epalrestat, according to one embodiment of the invention.
Figure 10D:
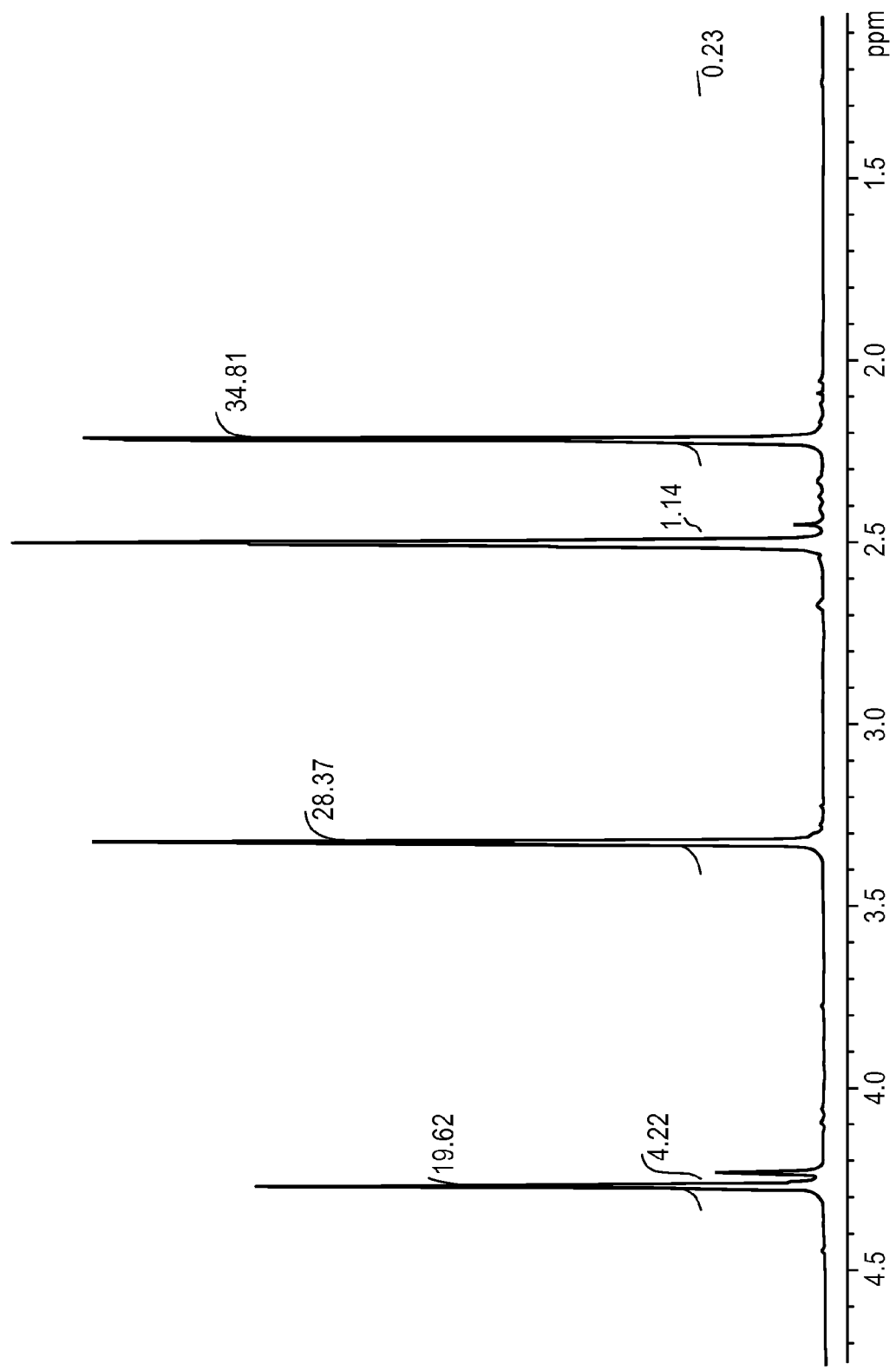
FIG. 10D is an $^1$H-NMR spectrum from 4.5 to 1.5 ppm of a crystalline sodium anhydrate salt of epalrestat, according to one embodiment of the invention.
Figure 11A:
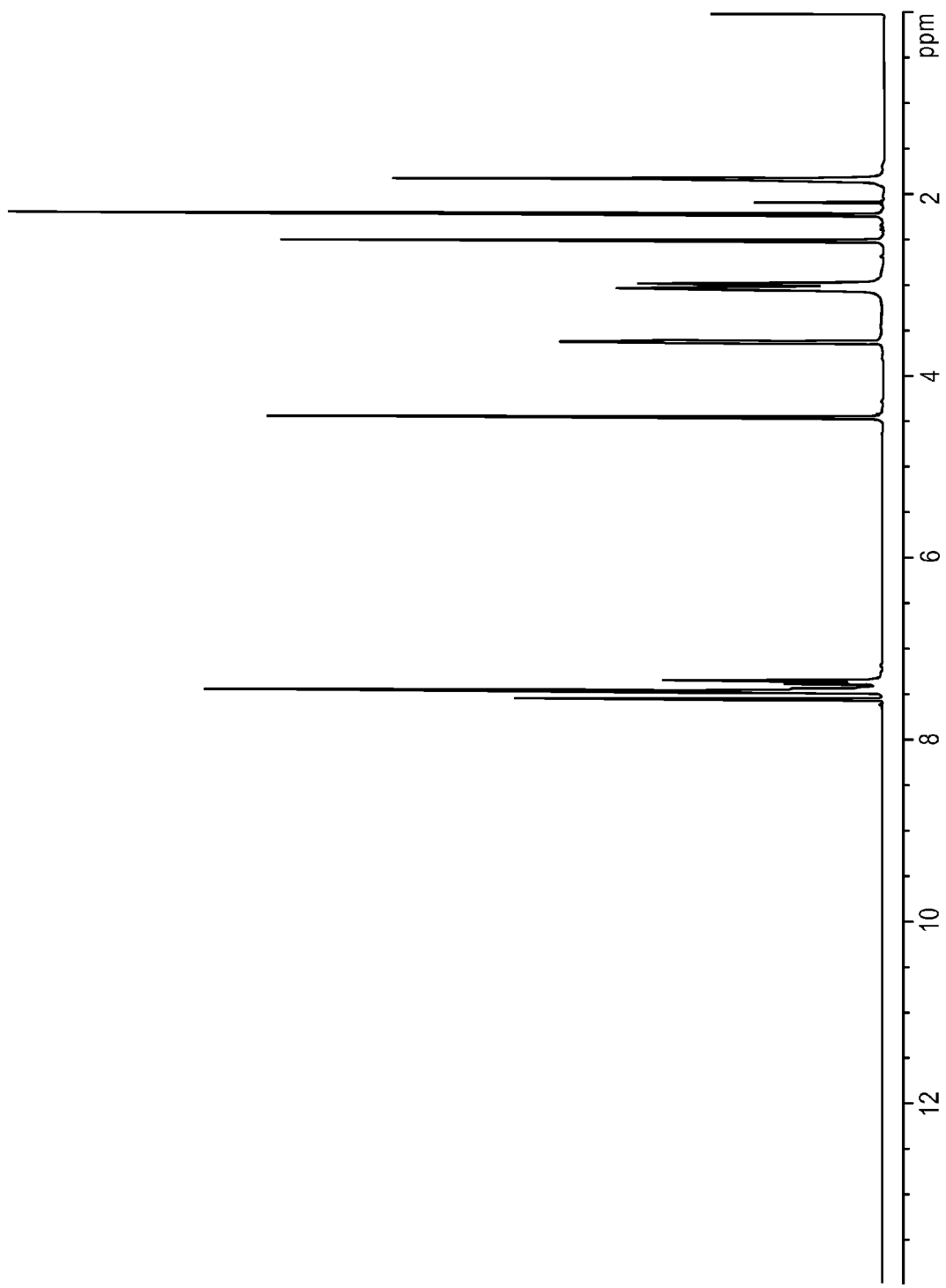
FIG. 11A is a full ¹H-NMR spectrum of a crystalline 1-(2-hydroxyethyl)-pyrrolidine anhydrate salt of epalrestat, according to one embodiment of the invention.
Figure 11B:
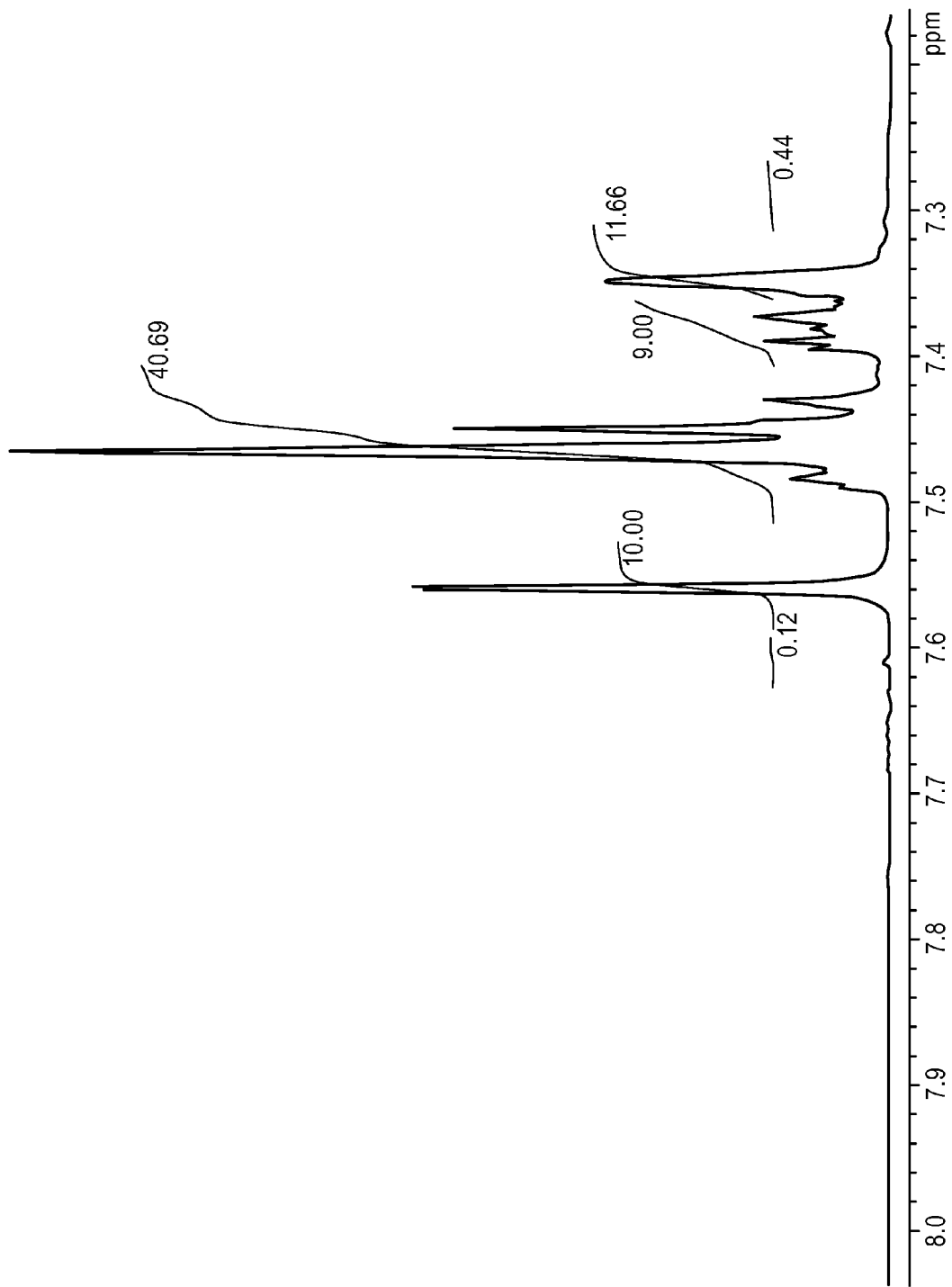
FIG. 11B is an ¹H-NMR spectrum from 8.0 to 7.2 ppm of a crystalline 1-(2-hydroxyethyl)-pyrrolidine anhydrate salt of epalrestat, according to one embodiment of the invention.
Figure 11C:
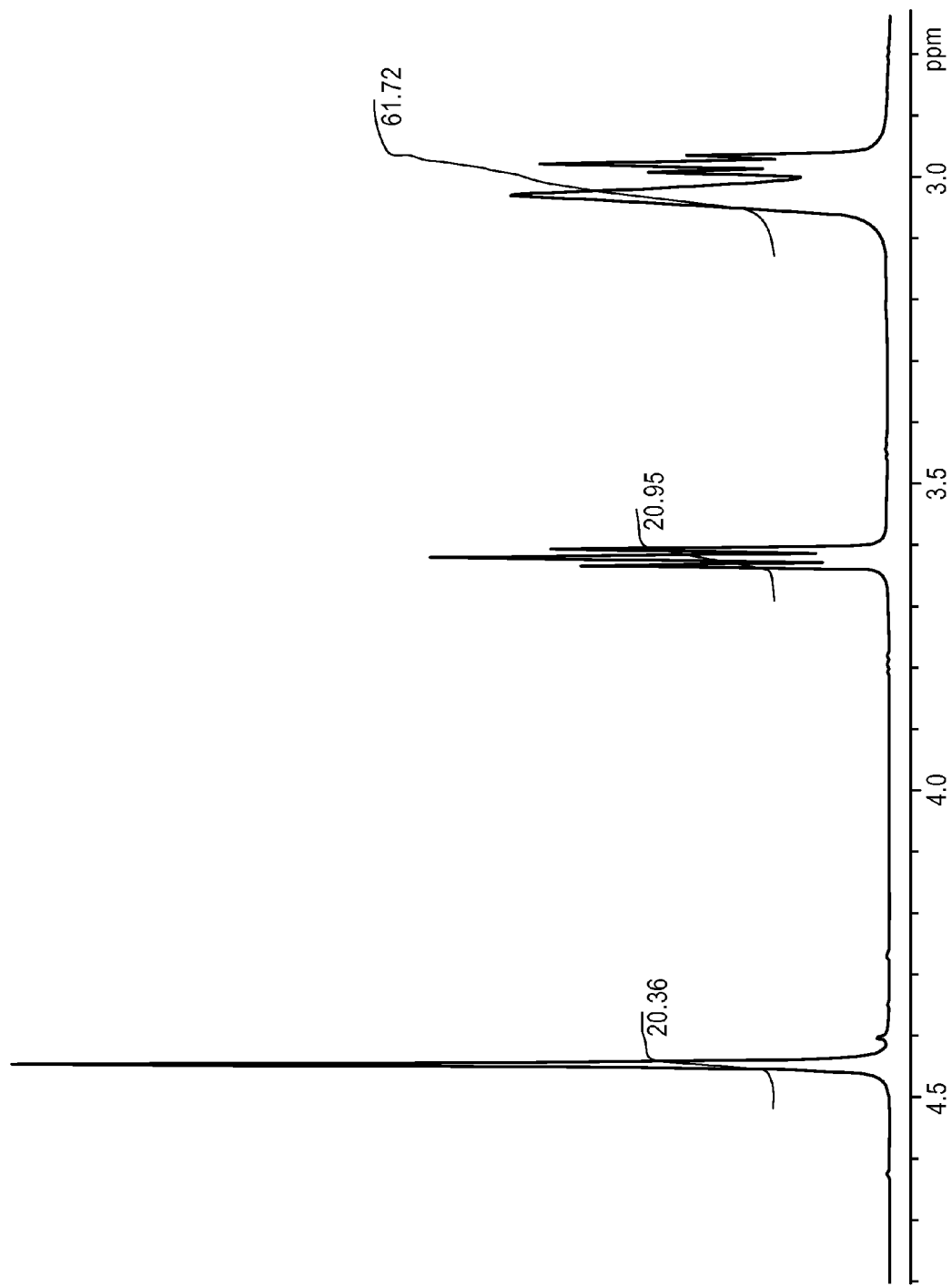
FIG. 11C is an ¹H-NMR spectrum from 4.8 to 2.8 ppm of a crystalline 1-(2-hydroxyethyl)-pyrrolidine anhydrate salt of epalrestat, according to one embodiment of the invention.
Figure 12A:
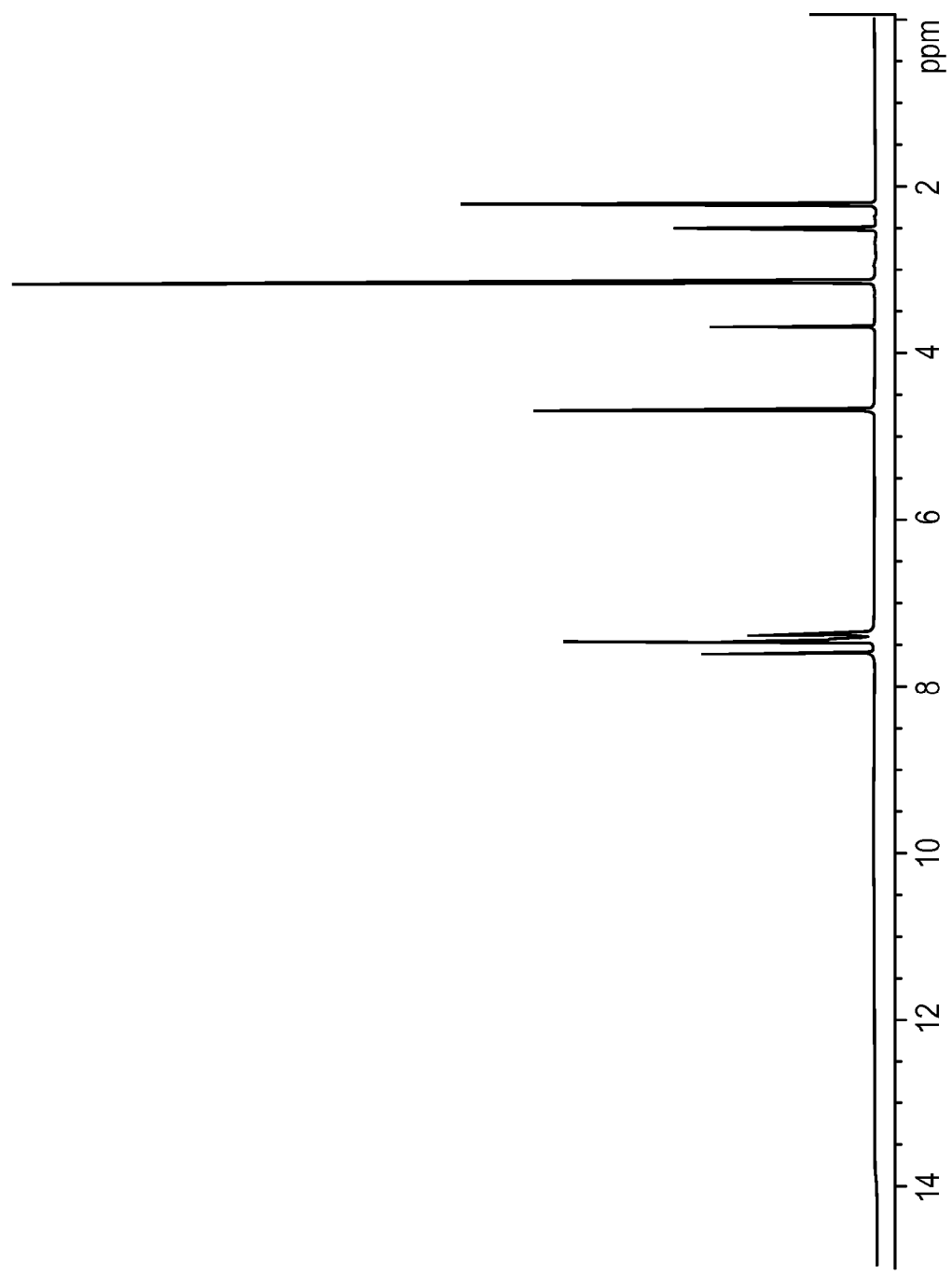
FIG. 12A is a full spectrum of a betaine hydrogen diacid cocrystal of epalrestat, according to one embodiment of the invention.
Figure 12B:
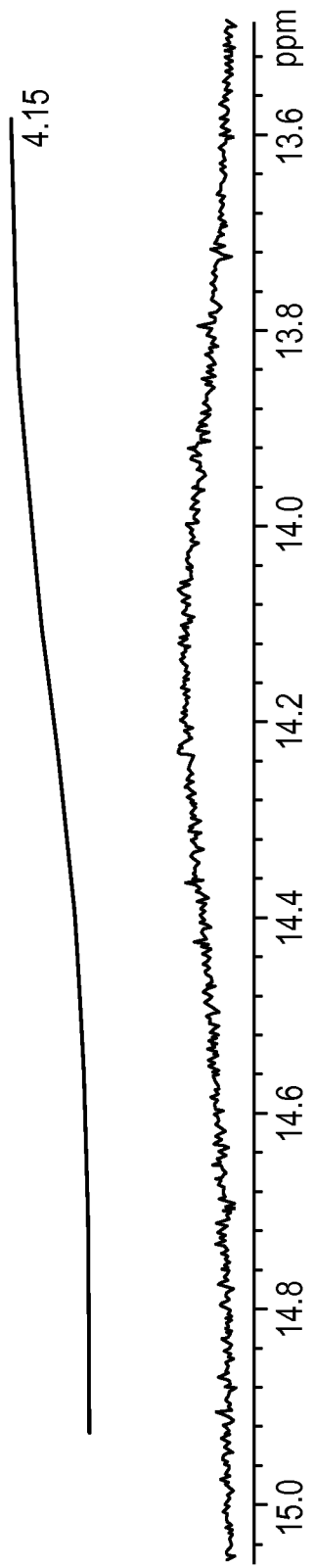
FIG. 12B is an ¹H-NMR spectrum from 15.0 to 13.6 ppm of a betaine hydrogen diacid cocrystal of epalrestat, according to one embodiment of the invention.
Figure 12C:
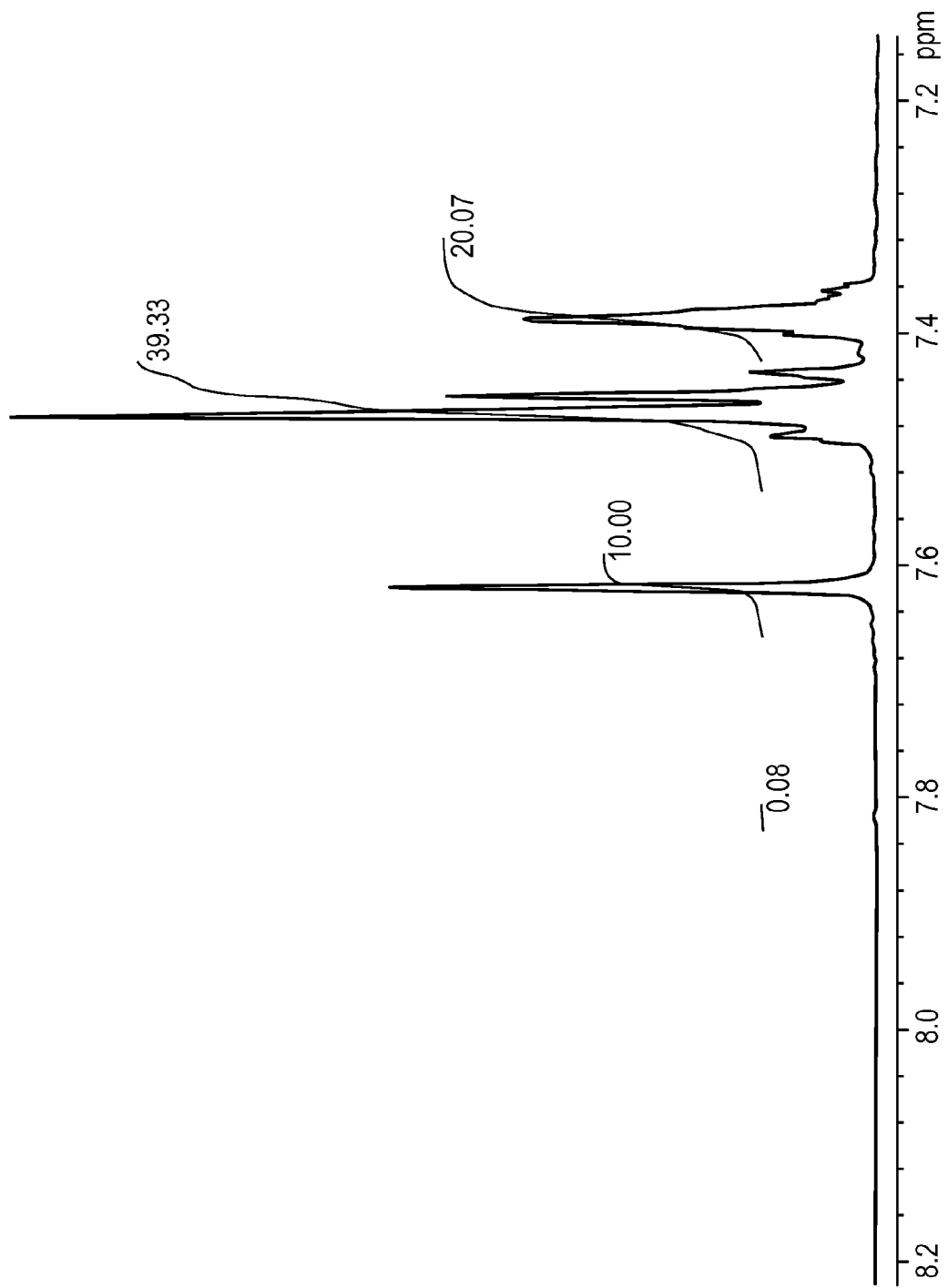
FIG. 12C is an ¹H-NMR spectrum from 8.2 to 7.2 ppm of a betaine hydrogen diacid cocrystal of epalrestat, according to one embodiment of the invention.
Figure 12D:
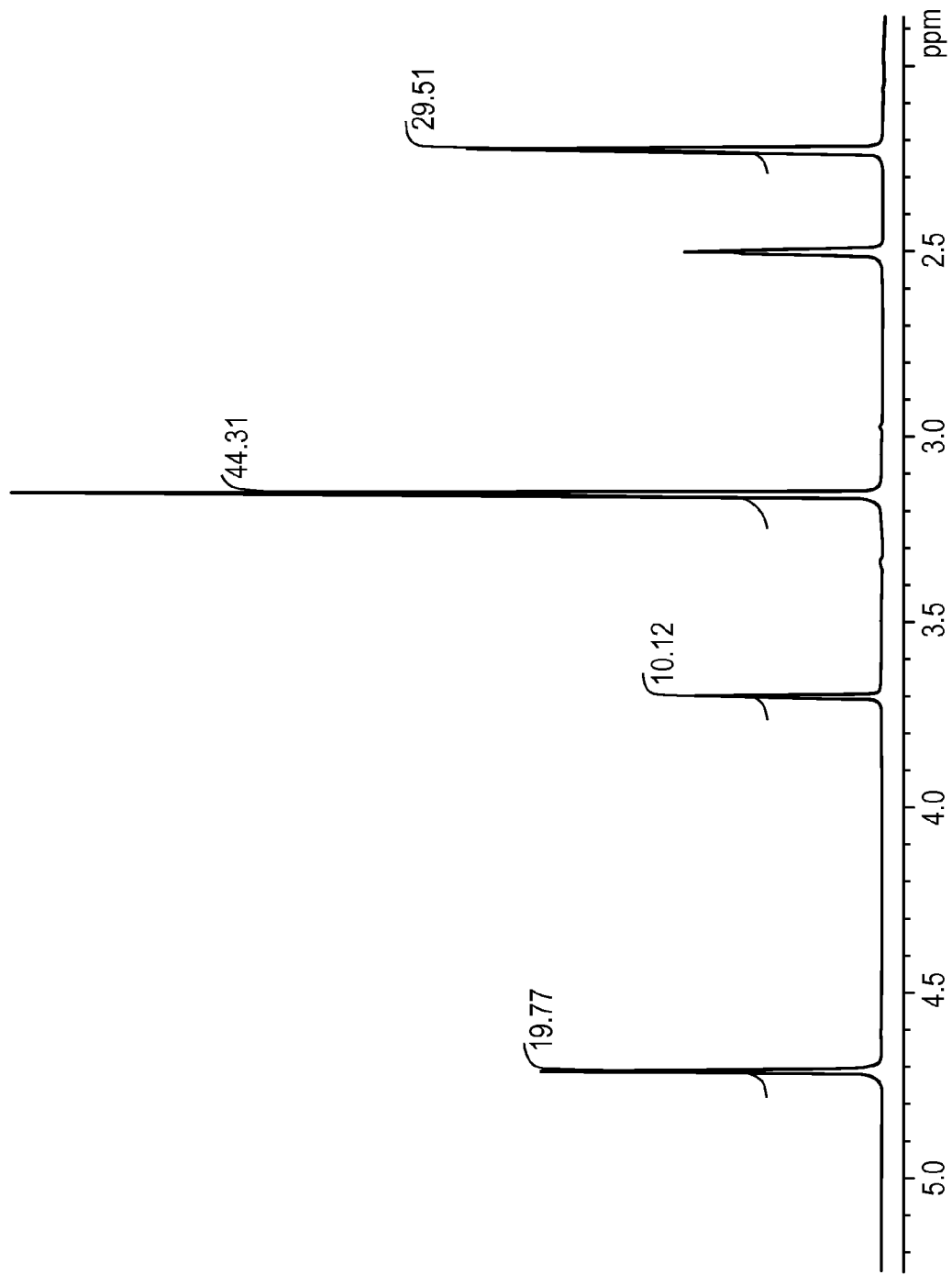
FIG. 12D is an ¹H-NMR spectrum from 5.2 to 2.0 ppm of a betaine hydrogen diacid cocrystal of epalrestat, according to one embodiment of the invention.
Figure 16:
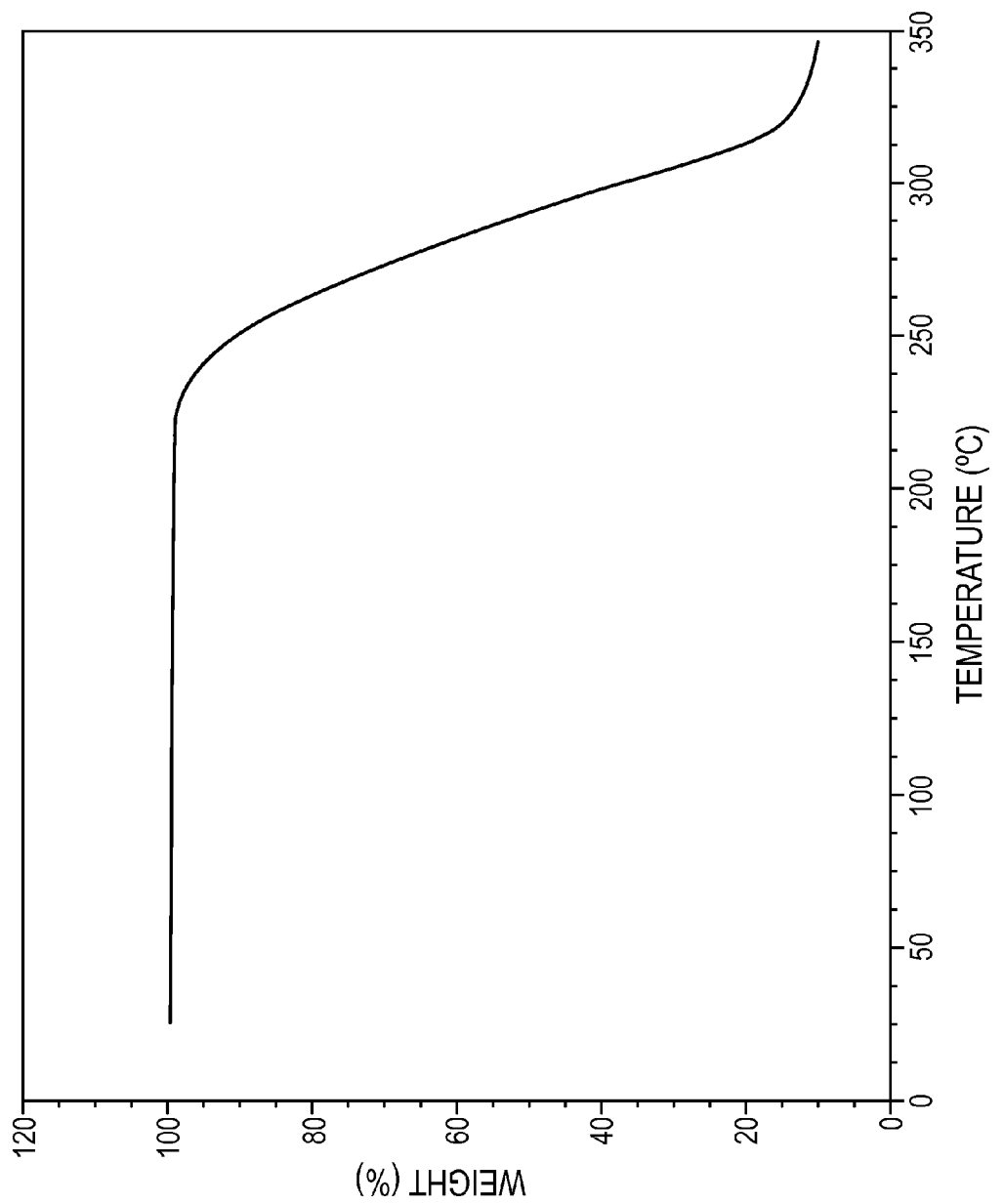
Figure 18A:
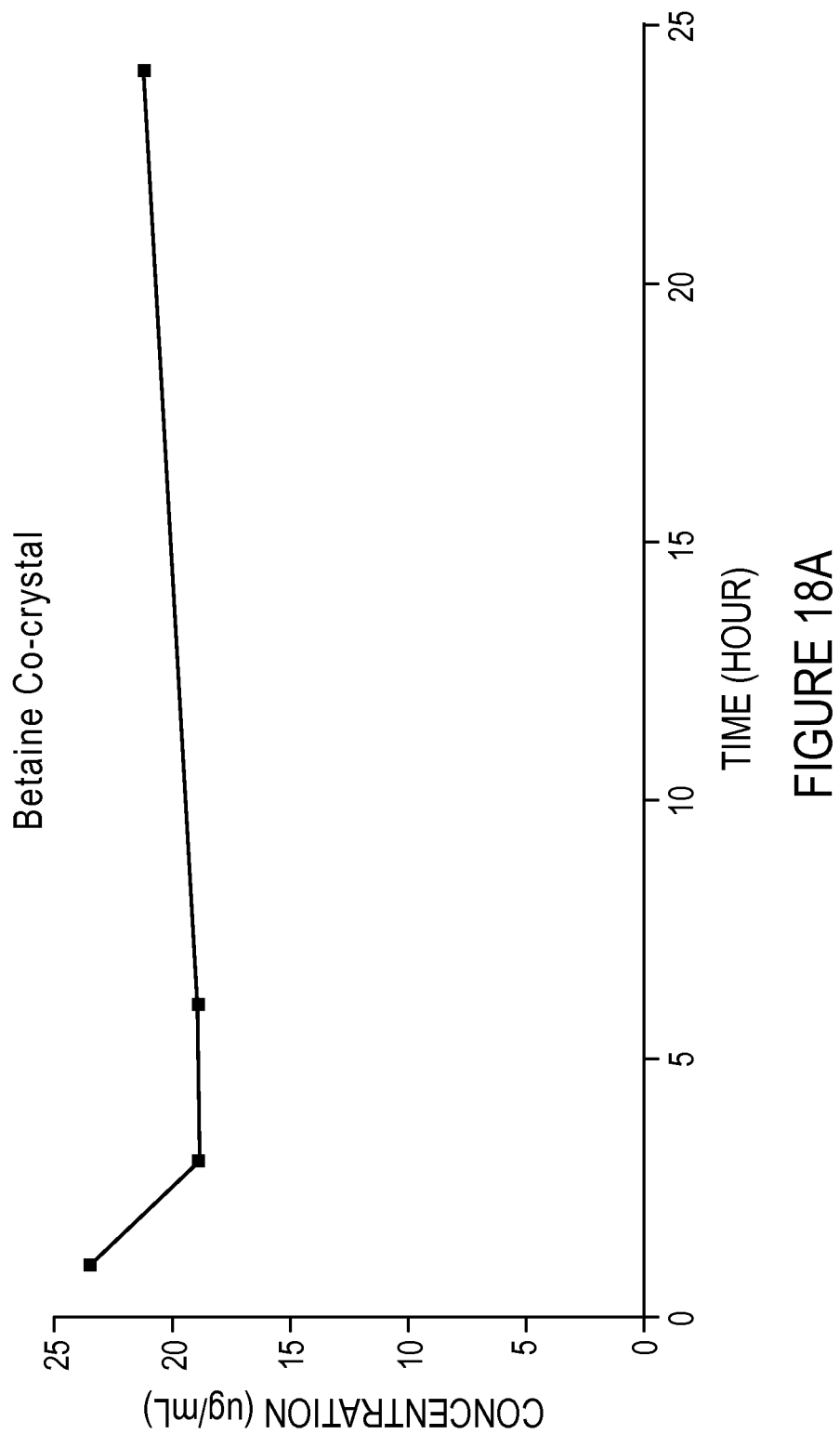
FIGS. 18A-18B show solubility data for a betaine hydrogen diacid cocrystal of epalrestat, according to one embodiment of the invention.

The novel betaine cocrystal of epalrestat is characterized by an XRPD pattern substantially as shown in FIG. 4, a DSC thermogram substantially as shown in FIG. 8, $^1$H-NMR spectra substantially as shown in FIGS. 12A-12D, a TGA profile substantially as shown in FIG. 16, and a solubility profile substantially as shown in FIG. 18A.

An exemplary listing of representative XRPD peaks of the novel betaine cocrystal of epalrestat according to the invention can be found in Table 7. Prominent XRPD peaks may include, in one exemplary embodiment, peaks at 6.0, 12.2, 13.1, 14.0, and 15.0 °2θ±0.2. An exemplary listing of representative NMR data can be found in Table 8.

TABLE 7

| °2θ | d space (Å) | Intensity (%) |
|---|---|---|
| 6.0 ± 0.2 | 14.71 ± 0.50 | 90 |
| 12.2 ± 0.2 | 7.23 ± 0.12 | 15 |
| 12.7 ± 0.2 | 6.95 ± 0.11 | 13 |
| 13.1 ± 0.2 | 6.76 ± 0.10 | 61 |
| 14.0 ± 0.2 | 6.33 ± 0.41 | 22 |
| 14.4 ± 0.2 | 6.13 ± 0.09 | 9 |
| 15.0 ± 0.2 | 5.91 ± 0.08 | 77 |
| 16.1 ± 0.2 | 5.51 ± 0.07 | 29 |
| 16.4 ± 0.2 | 5.42 ± 0.07 | 30 |
| 16.8 ± 0.2 | 5.27 ± 0.06 | 25 |
| 18.1 ± 0.2 | 4.91 ± 0.05 | 23 |
| 18.5 ± 0.2 | 4.79 ± 0.05 | 23 |
| 19.1 ± 0.2 | 4.65 ± 0.05 | 34 |
| 20.4 ± 0.2 | 4.35 ± 0.04 | 18 |
| 21.0 ± 0.2 | 4.24 ± 0.04 | 10 |
| 21.4 ± 0.2 | 4.15 ± 0.04 | 37 |
| 21.8 ± 0.2 | 4.08 ± 0.04 | 100 |
| 22.1 ± 0.2 | 4.02 ± 0.04 | 38 |
| 22.5 ± 0.2 | 3.95 ± 0.03 | 11 |
| 22.9 ± 0.2 | 3.88 ± 0.03 | 8 |
| 23.5 ± 0.2 | 3.78 ± 0.03 | 6 |
| 24.0 ± 0.2 | 3.72 ± 0.03 | 12 |
| 24.3 ± 0.2 | 3.66 ± 0.03 | 31 |
| 24.8 ± 0.2 | 3.60 ± 0.03 | 37 |

TABLE 7-continued

| °2θ | d space (Å) | Intensity (%) |
|---|---|---|
| 25.5 ± 0.2 | 3.49 ± 0.03 | 80 |
| 25.8 ± 0.2 | 3.45 ± 0.03 | 43 |
| 26.2 ± 0.2 | 3.40 ± 0.03 | 13 |
| 26.5 ± 0.2 | 3.36 ± 0.03 | 44 |
| 27.5 ± 0.2 | 3.24 ± 0.02 | 12 |
| 28.2 ± 0.2 | 3.17 ± 0.02 | 35 |
| 28.5 ± 0.2 | 3.13 ± 0.02 | 10 |
| 28.8 ± 0.2 | 3.10 ± 0.02 | 18 |
| 29.8 ± 0.2 | 3.00 ± 0.02 | 8 |

TABLE 8

| protons | peak position (ppm) | multiplicity | number of protons |
|---|---|---|---|
| CH$_3$ | 2.22 | singlet | 6 |
| CH$_3$ (betaine) | 3.15 | singlet | 9 |
| CH$_2$ (betaine) | 3.70 | singlet | 2 |
| CH$_2$ | 4.70 | singlet | 4 |
| olefin/aromatic | 7.36-7.40 | multiplet | 4 |
| olefin/aromatic | 7.43-7.49 | multiplet | 8 |
| olefin | 7.62 | singlet | 2 |

In various embodiments, the novel betaine cocrystal of epalrestat described herein is stable. For example, no change in the XRPD pattern was seen when the material was compressed into a disk at 3400 pounds of pressure (117 MPa pressure) for 1 minute, using a Carver hydraulic press and pellet die.

Pharmaceutical Compositions and Methods of Treatment and/or Prevention

The novel crystalline salt forms of epalrestat and novel betaine cocrystal of epalrestat according to various embodiments of the invention possess the same general pharmacological activity as epalrestat free acid, and are useful for treating and/or preventing diabetic complications such as those discussed above, including, for example, diabetic neuropathy, diabetic retinopathy, and diabetic nephropathy. By use of the term "treating" or "alleviating" it is meant decreasing the symptoms, markers, or any negative effects of a condition in any appreciable degree in a patient who currently has the condition, and by "preventing" it is meant preventing entirely or preventing to some extent, such as, for example, by delaying the onset or lessening the degree to which a patient develops the condition.

Accordingly, various embodiments of the invention include methods for preventing and/or treating cardiac tissue ischemia in a mammal comprising administering to said mammal an effective amount of epalrestat comprising one or more of the novel crystalline salt forms of epalrestat and/or the novel betaine cocrystal of epalrestat described herein. Various embodiments of the invention also include methods for treating and/or preventing cardiac tissue ischemia in a mammal comprising administering to said mammal a pharmaceutical composition comprising at least some amount of at least one novel crystalline salt form of epalrestat described herein and/or the novel betaine cocrystal of epalrestat described herein, and a pharmaceutically acceptable vehicle, carrier, and/or diluent. In exemplary methods, said mammal may be suffering from cardiac tissue ischemia or may be at risk of suffering from cardiac tissue ischemia. For example, a mammal at risk may be awaiting or undergoing cardiac, cardiovascular, or other major surgery. Thus, various embodiments of the invention include methods for providing myocardial protection during surgery or myocardial protection in patients presenting with ongoing cardiac or cerebral ischemic events or chronic cardioprotection in patients diagnosed with, or at risk for, coronary heart disease, cardiac dysfunction or myocardial stunning. As used herein, "mammal" is intended to include humans.

Various embodiments of the invention include methods of inhibiting aldose reductase in a mammal in need of inhibition of aldose reductase comprising administering an aldose reductase inhibiting amount of epalrestat comprising at least one of the novel crystalline salt forms of epalrestat and/or novel betaine cocrystal of epalrestat as described herein. Various embodiments of the invention also include methods of inhibiting aldose reductase in a mammal in need of inhibition of aldose reductase, comprising administering a pharmaceutical composition comprising at least one novel crystalline salt form of epalrestat and/or novel betaine cocrystal of epalrestat as described herein, and a pharmaceutically acceptable vehicle, carrier, and/or diluent.

Additional embodiments of the invention include methods of treating and/or preventing one or more diabetic complications in a mammal suffering from one or more diabetic complications comprising administering to said mammal an effective amount of epalrestat comprising at least one novel crystalline salt form of epalrestat and/or novel betaine cocrystal of epalrestat as described herein. Diabetic complications which may be treated and/or prevented by exemplary methods of the invention include, but are not limited to, diabetic neuropathy, diabetic nephropathy, diabetic cardiomyopathy, cardiac autonomic neuropathy, diabetic retinopathy, diabetic macular edema, diabetic gastroparesis, cataracts, foot ulcers, diabetic macroangiopathy, and diabetic microangiopathy. Various embodiments of the invention are also directed to methods of treating and/or preventing one or more diabetic complications in a mammal suffering from one or more diabetic complications comprising administering to said mammal an effective amount of a pharmaceutical composition as set forth herein.

Further embodiments of the invention contemplate methods of treating and/or preventing homocystinuria, and/or reducing levels of homocysteine in the blood serum, for example in a patient with diabetes, by administering an effective amount of epalrestat comprising the novel betaine cocrystal of epalrestat, or composition and/or formulation comprising an effective amount of epalrestat comprising the novel betaine cocrystal of epalrestat, as described herein. Betaine, also known as trimethylglycine or glycine betaine, is a naturally occurring molecule found in dietary sources (Olthof M R, Curr Drug Metab 2005; 6:15-22). In biological systems, betaine is important in the metabolism of homocysteine, and functions as a methyl donor. Betaine is therefore used therapeutically to reduce elevated homocysteine concentrations (van Guldener C et al, Expert Opinion on Pharmacotherapy 2001; 2:1449-1460), and is approved for use in the U.S. and Europe as a therapeutic agent to treat homocystinuria from genetic causes (Cystadane prescribing information, FDA; Cystadane product information, EMEA). Elevated homocysteine is associated with cardiovascular disease in both Type 2 diabetes (Hoogeveen E K et al, Arterioscler Thromb Vasc Biol 1998; 18:133-138) and in non-diabetic populations (Bostom A G et al, Arch Intern Med 1999; 159:1077-1080). Homocysteine is also elevated in patients with various non-cardiovascular diabetic complications, including diabetic nephropathy (Bostom A G et al, Arterioscler Thromb Vasc Biol 1997; 17:2554-2558), diabetic retinopathy (Brazionis L et al, Diabetes Care 2008; 31:50-56), and diabetic neuropathy (Ambrosch A et al, Diabetic Medicine 2001; 18:185-192). Administration of a novel betaine cocrystal of epalrestat may, therefore, have an additional beneficial therapeutic effect for treating these conditions. For example, administration of the combination of epalrestat and betaine as in the novel cocrystal of the invention, for example to a diabetic patient, may have a synergistic effect that is greater than the effects of administering epalrestat and/or betaine alone.

Various additional embodiments of the invention include methods of palliating neurological disorders and delaying development of neurological disorders by administering aldose reductase inhibitors, including the novel crystalline salts of epalrestat and/or novel betaine cocrystal of epalrestat described herein, in order to modulate neurotrophic factor-associated activity, especially CNTF-associated levels and activity, for example as disclosed in U.S. Pat. No. 6,696,407. These methods are useful, for example, for a condition or circumstance in which neurotrophic factor-associated activity is indicated, such as neurological disorders, including neurodegenerative disorders. A "neurological disorder" as used herein means an aberration from clinically normal neural cell activity (i.e., compromised neural cell activity) and includes, by way of example only, neurodegenerative disease (of the CNS and/or PNS), neuropathies associated with toxicity (neurotoxicity) such as chemotherapy (i.e., vincristine or cisplatin-induced motor neuropathy) and alcohol consumption, immune-mediated neurodiseases such as multiple sclerosis (MS) and Guillain-Barre syndrome, hereditary neuropathies such as Charcot-Marie-Tooth neuropathies [see Lebo et al. (1992) Am. J. Hum. Genet. 50:42-55], injury due to trauma, and compromised function due to senescence. Examples of neurodegenerative disorders include but are not limited to, Huntington's disease, amyotrophic lateral sclerosis (ALS), Alzheimer's disease, Parkinson's disease, and Shy-Drager syndrome. The methods may also be useful in delaying development of a neurological disorder, and thus may be used in individuals who show no overt signs of disease but are, for example, at risk of developing disease.

As discussed, additional embodiments of the invention relate to pharmaceutical compositions comprising a therapeutically effective amount of one or more novel crystalline salts of epalrestat and/or novel betaine cocrystal of epalrestat according to various embodiments of the invention and a pharmaceutically acceptable carrier or excipient. The novel crystalline salts of epalrestat and/or novel betaine cocrystal of epalrestat according to various embodiments of the invention have the same or similar pharmaceutical activity as previously reported for epalrestat free acid. Pharmaceutical compositions for the treatment and/or prevention of those conditions or disorders may contain some amount, for example a therapeutically effective amount, of one or more of the novel crystalline salts of epalrestat and/or novel betaine cocrystal of epalrestat described herein, as appropriate, e.g. for treatment of a patient with the particular condition or disorder. As a further example, the amount of the one or more of the novel crystalline salts of epalrestat and/or novel betaine cocrystal of epalrestat in the pharmaceutical compositions may likewise be lower than a therapeutically effective amount, and may, for example, be in the composition in conjunction with another compound or form of epalrestat which, when combined, are present in a therapeutically effective amount. A "therapeutically effective amount" as described herein refers to an amount of a therapeutic agent sufficient to treat, alleviate, and/or prevent a condition treatable and/or preventable by administration of a composition of the invention, in any degree. That amount can be an amount sufficient to exhibit a detectable therapeutic or preventative or ameliorative effect, and can be determined by routine experimentation by those of skill in the art. The effect may include, for example, treatment, alleviation, and/or prevention of the conditions listed herein. The actual amount required, e.g. for treatment of any particular patient, will depend upon a variety of factors including the disorder being treated and/or prevented; its severity; the specific pharmaceutical composition employed; the age, body weight, general health, gender, and diet of the patient; the mode of administration; the time of administration; the route of administration; the rate of excretion of epalrestat; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001.

A pharmaceutical composition according to various embodiments of the invention may be any pharmaceutical form which contains one or more novel crystalline salts of epalrestat and/or novel betaine cocrystal of epalrestat according to various embodiments of the invention. Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition according to various embodiments of the invention, that is one having one or more of the novel crystalline salts of epalrestat and/or novel betaine cocrystal of epalrestat described herein, a carrier may be chosen that maintains the crystalline salt form or cocrystal form. In other words, the carrier, in some embodiments, will not substantially alter the crystalline form of the crystalline salts of epalrestat or novel betaine cocrystal of epalrestat as described herein. In certain embodiments, the carrier will similarly not be otherwise incompatible with epalrestat itself, crystalline salts of epalrestat, or novel betaine cocrystal of epalrestat according to various embodiments of the invention, such as by producing any undesirable biological effect or otherwise interacting in a deleterious manner with any other component(s) of the pharmaceutical composition.

The pharmaceutical compositions according to various embodiments of the invention are optionally formulated in unit dosage form for ease of administration and uniformity of dosage. A "unit dosage form" refers to a physically discrete unit of therapeutic agent appropriate for the patient to be treated. It will be understood, however, that the total daily dosage of the novel crystalline salts of epalrestat and/or novel betaine cocrystal of epalrestat according to various embodiments of the invention and pharmaceutical compositions thereof will be decided by the attending physician within the scope of sound medical judgment using known methods.

Because the crystalline form of the novel crystalline salts of epalrestat and novel betaine cocrystal of epalrestat described herein is more easily maintained during preparation, solid dosage forms are a preferred form for the pharmaceutical composition of the invention. Solid dosage forms for oral administration may include, for example, capsules, tablets, pills, powders, and granules. In one exemplary embodiment, the solid dosage form is a tablet. The active ingredient may be contained in a solid dosage form formulation that provides quick release, sustained release, or delayed release after administration to the patient. In such solid dosage forms, the active compound may be mixed with at least one inert, pharmaceutically acceptable carrier, such as, for example, sodium citrate or dicalcium phosphate. The solid dosage form may also include one or more of various additional ingredients, including, for example: a) fillers or extenders such as, for example, starches, lactose, sucrose, glucose, mannitol, and silicic acid; b) binders such as, for example, carboxymethylcellulose, alginates, gelatin, polyvinylpyrrolidinone, sucrose, and acacia; c) humectants such as, for example, glycerol; d) disintegrating agents such as, for example, agar, calcium carbonate, potato or tapioca starch, alginic acid, certain silicates, and sodium carbonate; e) dissolution retarding agents such as, for example, paraffin; f) absorption accelerators such as, for example, quaternary ammonium compounds; g) wetting agents such as, for example, cetyl alcohol and glycerol monostearate; h) absorbents such as, for example, kaolin and bentonite clay; and i) lubricants such as, for example, talc, calcium stearate, magnesium stearate, solid polyethylene glycols, and sodium lauryl sulfate. The solid dosage forms may also comprise buffering agents. They may optionally contain opacifying agents and can also be of a composition that they release the active ingredient(s) only, or preferentially, in a certain part of the intestinal tract, optionally, in a delayed manner. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Solid dosage forms of pharmaceutical compositions according to various embodiments of the invention can also be prepared with coatings and shells such as enteric coatings and other coatings well known in the pharmaceutical formulating art.

The novel crystalline salts of epalrestat and novel betaine cocrystal of epalrestat according to various embodiments of the invention can be, for example, administered in a solid micro-encapsulated form with one or more carriers as discussed above. Microencapsulated forms may also be used in soft and hard-filled gelatin capsules with carriers such as lactose or milk sugar as well as high molecular weight polyethylene glycols and the like.

The novel crystalline salts of epalrestat and novel betaine cocrystal of epalrestat according to various embodiments of the invention may also be used in the preparation of non-solid formulations, e.g., injectables and patches, of epalrestat. Such non-solid formulations are known in the art. In a non-solid formulation, the crystalline salt form and/or cocrystal form may, in certain exemplary embodiments, not be maintained. For example, the crystalline salt form may be dissolved in a liquid carrier. In this case, the novel crystalline salts of epalrestat and/or novel betaine cocrystal of epalrestat according to various embodiments of the invention may represent intermediate forms of epalrestat used in the preparation of the non-solid formulation. The novel crystalline salts of epalrestat and novel betaine cocrystal of epalrestat according to various embodiments of the invention may provide advantages of handling stability and/or purity to the process of making such formulations.

The invention also relates to the treatment and/or prevention of diabetes-associated disorders such as those discussed above. The invention provides methods for treating and/or preventing diabetes-associated disorders by administering to mammals epalrestat comprising one or more of the novel crystalline salt forms of epalrestat and/or novel betaine cocrystal of epalrestat as described herein, or a pharmaceutical composition containing the same, in an amount sufficient to treat and/or prevent a condition treatable and/or preventable by administration of a composition of the invention. That amount is the amount sufficient to exhibit any detectable therapeutic and/or preventative or ameliorative effect. The effect may include, for example, treatment and/or prevention of the conditions listed herein. These novel crystalline salt forms of epalrestat and novel betaine cocrystal of epalrestat and pharmaceutical compositions containing them may, according to various embodiments of the invention, be administered using any amount, any form of pharmaceutical composition, and any route of administration effective, e.g. for treatment, all of which are easily determined by those of skill in the art through routine experimentation. After formulation with an appropriate pharmaceutically acceptable carrier in a desired dosage, as known by those of skill in the art, the pharmaceutical compositions can be administered to humans and other mammals by any known method, such as, for example, orally, rectally, or topically (such as by powders or other solid form-based topical formulations). In certain embodiments, the novel crystalline salt forms of epalrestat and novel betaine cocrystal of epalrestat according to various embodiments of the invention may be administered at dosage levels ranging from about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than about 0.001 mg/kg or greater than about 50 mg/kg (for example, ranging from about 50 mg/kg to about 100 mg/kg) can also be administered to a subject in certain embodiments of the invention. As discussed above, the amount required for a particular patient will depend upon a variety of factors including the disorder being treated and/or prevented; its severity; the specific pharmaceutical composition employed; the age, body weight, general health, gender, and diet of the patient; the mode of administration; the time of administration; the route of administration; and the rate of excretion of epalrestat; the duration of the treatment; any drugs used in combination or coincidental with the specific compound employed; and other such factors well known in the medical arts. And, as also discussed, the pharmaceutical composition of the novel crystalline salts of epalrestat and/or novel betaine cocrystal of epalrestat as described herein may be administered as a unit dosage form.

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

EXAMPLES

Example 1

Preparation of a Crystalline Potassium Anhydrate Salt of Epalrestat

A mixture of 2.78 grams (8.70 mmol) of epalrestat free acid, 150 mL of absolute ethanol, and a solution of 855 mg (8.71 mmol) of potassium acetate in 25 mL of absolute ethanol was placed in a sonication bath for about 1 minute and stirred for about 10 minutes. Undissolved solid was collected by vacuum filtration and was dried in a vacuum oven at ambient temperature overnight to give 2.80 g (7.83 mmol, 90% yield) of the crystalline potassium anhydrate salt of epalrestat. Analytical data were obtained on the final product: the XRPD pattern was as shown in FIG. 1, the DSC thermogram was as shown in FIG. 5, the $^1$H-NMR spectrum was as shown in FIGS. 9A-9D, and the TGA profile was as shown in FIG. 13.

Example 2

Preparation of a Crystalline Sodium Anhydrate Salt of Epalrestat

A solution of 211 mg (0.661 mmol) of epalrestat free acid in 11 mL of acetone was treated with 2.64 mL of a solution of 126 mg of sodium bicarbonate in 4 mL of water and 2 mL of acetone (55.4 mg, 0.659 mmol of sodium bicarbonate). Precipitation occurred and the solid was collected by filtration and allowed to dry in the air to give 216 mg (0.633 mmol, 96% yield) of the crystalline sodium anhydrate salt of epalrestat. Analytical data were obtained on the final product: the XRPD pattern was as shown in FIG. 2, the DSC thermogram was as shown in FIG. 6, the $^1$H-NMR spectrum was as shown in FIGS. 10A-10D, and the TGA profile was as shown in FIG. 14.

Example 3

Preparation of a Crystalline Sodium Anhydrate Salt of Epalrestat

A mixture of solution containing 3.08 g (9.64 mmol) of epalrestat free acid, 50 mL of methanol, and 3.75 mL of a solution of 516 mg of sodium hydroxide in 5 mL of water (387 mg, 9.68 mmol of sodium hydroxide) was briefly placed in an ultrasonic bath and stirred for 10 minutes. Undissolved solid was collected by vacuum filtration and dried in a vacuum oven at ambient temperature overnight to give 3.10 g (9.08 mmol, 94% yield) of the crystalline sodium anhydrate salt of epalrestat. Analytical data were obtained on the final product: the XRPD pattern was substantially as shown in FIG. 2, the DSC thermogram was substantially as shown in FIG. 6, the $^1$H-NMR spectrum was substantially as shown in FIGS. 10A-10D, and the TGA profile was substantially as shown in FIG. 14.

Example 4

Preparation of a crystalline 1-(2-hydroxyethyl)-pyrrolidine Anhydrate Salt of Epalrestat A solution of 216 mg (0.676 mmol) of epalrestat in 15 mL of acetone was treated with 82.1 µL of 1-(2-hydroxyethyl)-pyrrolidine. Crystallization occurred after about 45 seconds and the resulting solid was collected by filtration to give the crystalline 1-(2-hydroxyethyl)-pyrrolidine anhydrate salt of epalrestat. Analytical data were obtained on the final product: the XRPD pattern was as shown in FIG. 3, the DSC thermogram was as shown in FIG. 7, the $^1$H-NMR spectrum was as shown in FIGS. 11A-11D, and the TGA profile was as shown in FIG. 15.

Example 5

Preparation of a Betaine Hydrogen Diacid Cocrystal of Epalrestat

Figure 17:
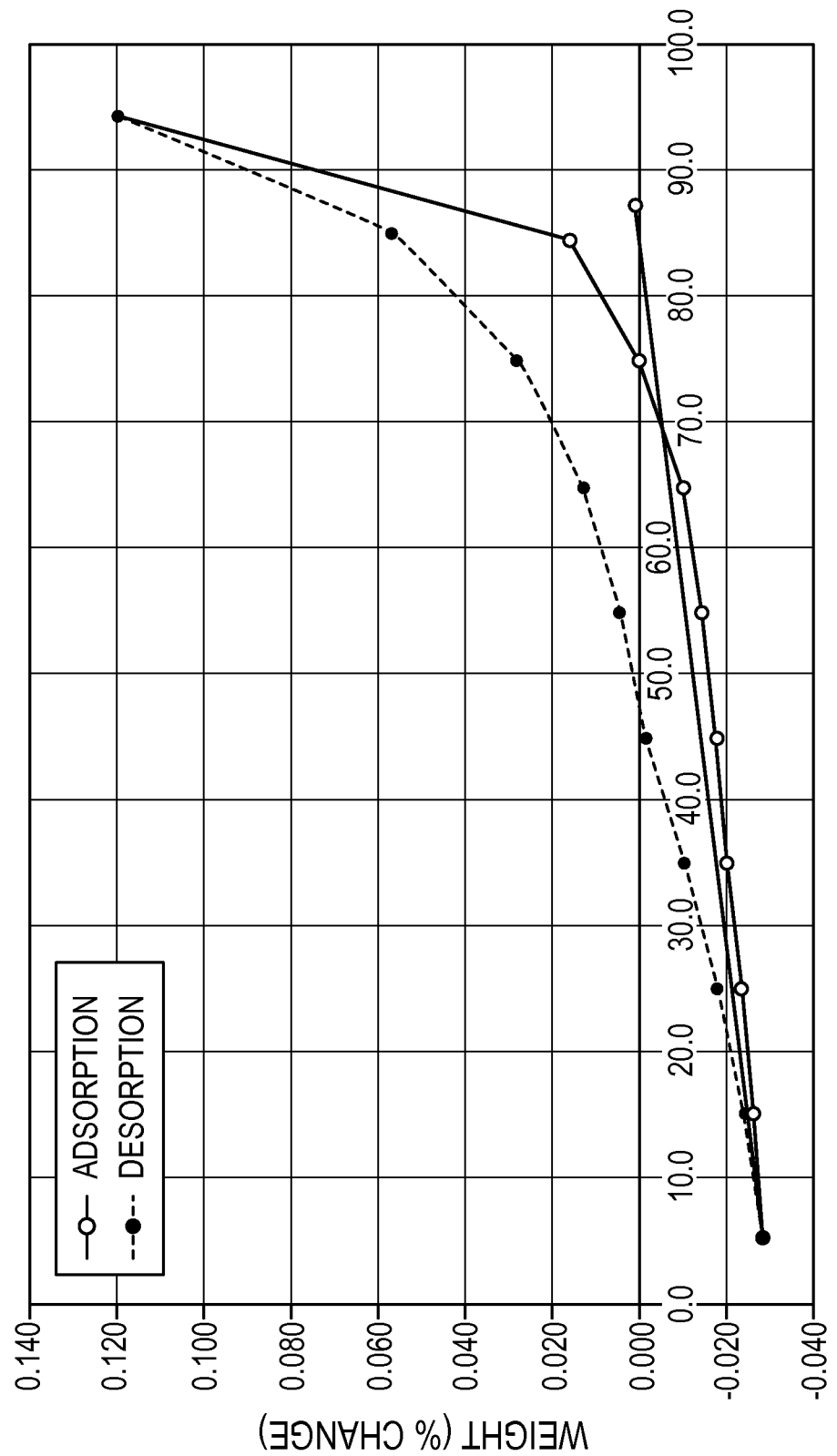
FIG. 17 is a DVS profile of a betaine hydrogen diacid cocrystal of epalrestat, according to one embodiment of the invention.

A mixture of 176 mg (0.551 mmol) of epalrestat free acid and 10 mL of methanol was treated with 2.8 mL of a solution of 91 mg of betaine in 4 mL of methanol (64 mg, 0.546 mmol of betaine). The sample began to clear (dissolve) and then became hazy. Precipitation occurred and the solid was collected by filtration and allowed to dry in the air to give 124.5 mg (60% yield) of betaine hydrogen diepalrestat. The crystals obtained were birefringent, yellow, fine blades. Analytical data were obtained on the final product: the XRPD pattern was as shown in FIG. 4, the DSC thermogram was as shown in FIG. 8, the $^1$H-NMR spectrum was as shown in FIGS. 12A-12D, the TGA profile was as shown in FIG. 16, and the DVS profile was substantially as shown in FIG. 17.

Example 6

Preparation of a Betaine Hydrogen Diacid Cocrystal of Epalrestat

A mixture of 2.10 grams (6.56 mmol) of epalrestat free acid, 769 mg (6.56 mmol) of betaine, and 150 mL of methanol was stirred for 10 minutes. Undissolved solid was collected by vacuum filtration at ambient temperature and were dried overnight in a vacuum oven under reduced pressure to give 2.08 g (84% yield) of betaine hydrogen diepalrestat. The crystals obtained were fine blades, micaceous particles, and rhombohedrals, yellow-orange in color. Analytical data were obtained on the final product: the XRPD pattern was substantially as shown in FIG. 4, the DSC thermogram was substantially as shown in FIG. 8, the $^1$H-NMR spectrum was substantially as shown in FIGS. 12A-12D, the TGA profile was substantially as shown in FIG. 16, and the DVS profile was as shown in FIG. 17. Elemental analysis was as follows:

| | % C | % H | % N | % S |
|---|---|---|---|---|
| Betaine (experimental) | 55.56 | 4.88 | 5.56 | 17.16 |
| Betaine theoretical | 55.68 | 4.81 | 5.57 | 16.99 |

Example 7

Preparation of a Betaine Hydrogen Diacid Cocrystal of Epalrestat

A solution of 91 mg (0.29 mmol) of epalrestat free acid, 33 mg (0.28 mg) of betaine, 0.10 mL of water, and 3 mL of THF was left in a fume hood until the solvents had evaporated. The remaining solid was found to be betaine hydrogen diepalrestat by XRPD analysis. An XRPD pattern obtained on the final product was substantially as shown in FIG. 4.

Example 8

Preparation of a Betaine Hydrogen Diacid Cocrystal of Epalrestat

Figure 18B:
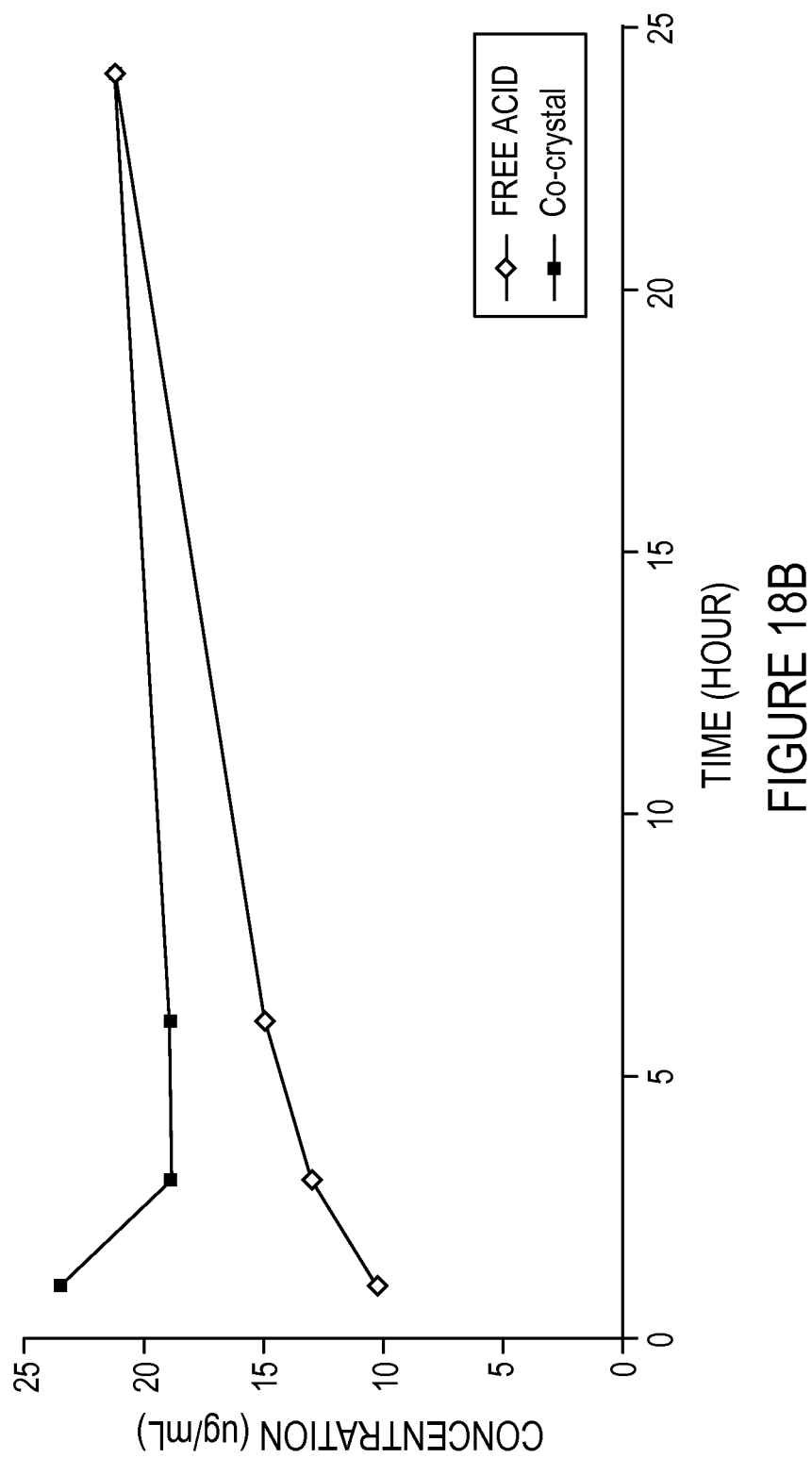

A solution of 2.17 g of betaine in 100 mL of methanol was added to 1.48 g of epalrestat and the resulting slurry was sonicated for 3 minutes. The yellow solids were collected by filtration, rinsed twice with methanol, and dried under reduced pressure to give 1.46 g of betaine hydrogen diepalrestat. The crystals obtained were yellow and birefringent. Analytical data were obtained on the final product: the XRPD pattern was substantially as shown in FIG. 4 and the $^1$H-NMR spectrum was substantially as shown in FIGS. 12A-12D. Solubility data were obtained in water on the final product, and the solubility profile is shown in FIG. 18A. As can be seen in FIG. 18B, epalrestat dissolves more quickly in water from the betaine hydrogen diacid cocrystal than it does from the free acid.

What is claimed is:

1. A crystalline potassium anhydrate salt of 5-[(1Z,2E)-2-methyl-3-phenylpropenylidene]-4-oxo-2-thioxo-3-thiazolidineacetic acid.

2. The crystalline potassium anhydrate salt of 5-[(1Z,2E)-2-methyl-3-phenylpropenylidene]-4-oxo-2-thioxo-3-thiazolidineacetic acid of claim 1, having substantially the same XRPD pattern as in FIG. 1.

3. A pharmaceutical composition comprising the crystalline potassium anhydrate salt of 5-[(1Z,2E)-2-methyl-3-phenylpropenylidene]-4-oxo-2-thioxo-3-thiazolidineacetic acid according to claim 1.

4. A method of treating and/or delaying development any of the following conditions in a mammal, comprising administering a pharmaceutical composition comprising the crystalline potassium anhydrate salt of 5-[(1Z,2E)-2-methyl-3-phenylpropenylidene]-4-oxo-2-thioxo-3-thiazolidineacetic acid according to claim 1: cardiac tissue ischemia, diabetic neuropathy, diabetic nephropathy, diabetic cardiomyopathy, cardiac autonomic neuropathy, diabetic retinopathy, diabetic macular edema, diabetic gastroparesis, cataracts, foot ulcers, diabetic macroangiopathy, and diabetic microangiopathy.

5. A method of inhibiting aldose reductase in a mammal in need thereof, comprising administering a pharmaceutical composition comprising the crystalline potassium anhydrate salt of 5-[(1Z,2E)-2-methyl-3-phenylpropenylidene]-4-oxo-2-thioxo-3-thiazolidineacetic acid according to claim 1.

6. A crystalline sodium anhydrate salt of 5-[(1Z,2E)-2-methyl-3-phenylpropenylidene]-4-oxo-2-thioxo-3-thiazolidineacetic acid.

7. The crystalline sodium anhydrate salt of 5-[(1Z,2E)-2-methyl-3-phenylpropenylidene]-4-oxo-2-thioxo-3-thiazolidineacetic acid of claim 6, having substantially the same XRPD pattern as in FIG. 2.

8. A pharmaceutical composition comprising the crystalline sodium anhydrate salt of 5-[(1Z,2E)-2-methyl-3-phenylpropenylidene]-4-oxo-2-thioxo-3-thiazolidineacetic acid according to claim 6.

9. A method of treating and/or delaying development any of the following conditions in a mammal, comprising administering a pharmaceutical composition comprising the crystalline sodium anhydrate salt of 5-[(1Z,2E)-2-methyl-3-phenylpropenylidene]-4-oxo-2-thioxo-3-thiazolidineacetic acid according to claim 6: cardiac tissue ischemia, diabetic neuropathy, diabetic nephropathy, diabetic cardiomyopathy, cardiac autonomic neuropathy, diabetic retinopathy, diabetic macular edema, diabetic gastroparesis, cataracts, foot ulcers, diabetic macroangiopathy, and diabetic microangiopathy.

10. A method of inhibiting aldose reductase in a mammal in need thereof, comprising administering a pharmaceutical composition comprising the crystalline sodium anhydrate salt of 5-[(1Z,2E)-2-methyl-3-phenylpropenylidene]-4-oxo-2-thioxo-3-thiazolidineacetic acid according to claim 6.

11. A crystalline 1-(2-hydroxyethyl)-pyrrolidine anhydrate salt of 5-[(1Z,2E)-2-methyl-3-phenylpropenylidene]-4-oxo-2-thioxo-3-thiazolidineacetic acid.

12. The crystalline 1-(2-hydroxyethyl)-pyrrolidine anhydrate salt of 5-[(1Z,2E)-2-methyl-3-phenylpropenylidene]-4-oxo-2-thioxo-3-thiazolidineacetic acid of claim 11, having substantially the same XRPD pattern as in FIG. 3.

13. A pharmaceutical composition comprising the crystalline 1-(2-hydroxyethyl)-pyrrolidine anhydrate salt of 5-[(1Z,2E)-2-methyl-3-phenylpropenylidene]-4-oxo-2-thioxo-3-thiazolidineacetic acid according to claim 11.

14. A method of treating and/or delaying development any of the following conditions in a mammal, comprising administering a pharmaceutical composition comprising the crystalline 1-(2-hydroxyethyl)-pyrrolidine anhydrate salt of 5-[(1Z,2E)-2-methyl-3-phenylpropenylidene]-4-oxo-2-thioxo-3-thiazolidineacetic acid according to claim 11: cardiac tissue ischemia, diabetic neuropathy, diabetic nephropathy, diabetic cardiomyopathy, cardiac autonomic neuropathy, diabetic retinopathy, diabetic macular edema, diabetic gastroparesis, cataracts, foot ulcers, diabetic macroangiopathy, and diabetic microangiopathy.

15. A method of inhibiting aldose reductase in a mammal in need thereof, comprising administering a pharmaceutical composition comprising the crystalline 1-(2-hydroxyethyl)-pyrrolidine anhydrate salt of 5-[(1Z,2E)-2-methyl-3-phenylpropenylidene]-4-oxo-2-thioxo-3-thiazolidineacetic acid according to claim 11.

16. A betaine hydrogen diacid cocrystal of 5-[(1Z,2E)-2-methyl-3-phenylpropenylidene]-4-oxo-2-thioxo-3-thiazolidineacetic acid.

17. The betaine hydrogen diacid cocrystal of 5-[(1Z,2E)-2-methyl-3-phenylpropenylidene]-4-oxo-2-thioxo-3-thiazolidineacetic acid of claim 16, having substantially the same XRPD pattern as in FIG. 4.

18. A pharmaceutical composition comprising the betaine hydrogen diacid cocrystal of 5-[(1Z,2E)-2-methyl-3-phenylpropenylidene]-4-oxo-2-thioxo-3-thiazolidineacetic acid according to claim 16.

19. A method of treating and/or delaying development any of the following conditions in a mammal, comprising administering a pharmaceutical composition comprising the betaine hydrogen diacid cocrystal of 5-[(1Z,2E)-2-methyl-3-phenylpropenylidene]-4-oxo-2-thioxo-3-thiazolidineacetic acid according to claim 16: cardiac tissue ischemia, diabetic neuropathy, diabetic nephropathy, diabetic cardiomyopathy, cardiac autonomic neuropathy, diabetic retinopathy, diabetic macular edema, diabetic gastroparesis, cataracts, foot ulcers, diabetic macroangiopathy, and diabetic microangiopathy.

20. A method of inhibiting aldose reductase in a mammal in need thereof, comprising administering a pharmaceutical composition comprising the betaine hydrogen diacid cocrystal of 5-[(1Z,2E)-2-methyl-3-phenylpropenylidene]-4-oxo-2-thioxo-3-thiazolidineacetic acid according to claim 16.

21. A method of treating homocystinuria, and/or reducing levels of homocysteine in blood serum, in a mammal in need thereof, comprising administering a pharmaceutical composition comprising the betaine hydrogen diacid cocrystal of 5-[(1Z,2E)-2-methyl-3-phenylpropenylidene]-4-oxo-2-thioxo-3-thiazolidineacetic acid according to claim 16.

* * * * *